US 8,481,679 B2

(12) United States Patent
Johnston et al.

(10) Patent No.: US 8,481,679 B2
(45) Date of Patent: Jul. 9, 2013

(54) IMMOBILIZING AN ENTITY IN A DESIRED ORIENTATION ON A SUPPORT MATERIAL

(75) Inventors: Stephen A Johnston, Tempe, AZ (US); Christopher W Diehnelt, Tempe, AZ (US)

(73) Assignee: Arizona Board of Regents Acting on behalf of Arizona State University, Scottsdale, AZ (US)

(*) Notice: Subject to any disclaimer, the term of this patent is extended or adjusted under 35 U.S.C. 154(b) by 512 days.

(21) Appl. No.: 12/677,782

(22) PCT Filed: Sep. 19, 2008

(86) PCT No.: PCT/US2008/010898
§ 371 (c)(1),
(2), (4) Date: May 26, 2010

(87) PCT Pub. No.: WO2009/082417
PCT Pub. Date: Jul. 2, 2009

(65) Prior Publication Data
US 2010/0248977 A1    Sep. 30, 2010

Related U.S. Application Data

(60) Provisional application No. 60/973,974, filed on Sep. 20, 2007.

(51) Int. Cl.
*C07K 7/00* (2006.01)
*A61K 38/04* (2006.01)

(52) U.S. Cl.
USPC .................. 530/326; 930/310; 427/207.1

(58) Field of Classification Search
USPC ................. 530/326; 930/10, 310; 427/207.1
See application file for complete search history.

(56) References Cited

U.S. PATENT DOCUMENTS

| 4,888,285 | A | 12/1989 | Nishimura |
| 5,252,719 | A | 10/1993 | Takeda |
| 5,766,908 | A | 6/1998 | Klein |
| 6,773,928 | B1 | 8/2004 | Yin |
| 7,078,192 | B2 | 7/2006 | Linder |
| 7,105,488 | B1 | 9/2006 | Tarasova |
| 2003/0175918 | A1 | 9/2003 | Basheer |
| 2004/0014242 | A1 | 1/2004 | Iwakura |
| 2006/0003381 | A1 | 1/2006 | Gilmore |
| 2010/0173377 | A1 | 7/2010 | Benson |

FOREIGN PATENT DOCUMENTS

| EP | 08864466.1 | 7/2010 |
| KR | 940005581 | 6/1994 |
| WO | WO 92/08788 | 5/1992 |

(Continued)

OTHER PUBLICATIONS

Eggenweiler, H-M, Linkers for solid-phase synthesis of small molecules: coupling and cleavage techniques, Drug Discovery Today 3 552-560 (1998) USA.

(Continued)

*Primary Examiner* — Ardin Marschel
*Assistant Examiner* — Jeremy C Flinders
(74) *Attorney, Agent, or Firm* — Quarles & Brady LLP; Gavin J. Milczarek-Desai

(57) ABSTRACT

The present invention relates to the identification and selection of attachment molecules that attach/immobilize an entity having a detectable activity or property on a support in an orientation that provides a detectable activity or property, and to surfaces made of the attachment molecules.

2 Claims, 19 Drawing Sheets

FOREIGN PATENT DOCUMENTS

| WO | WO 95/09058 | 4/1995 |
|---|---|---|
| WO | WO 0061789 | 10/2000 |
| WO | WO 2004090154 | 10/2004 |
| WO | WO 2009/082417 | 7/2009 |

OTHER PUBLICATIONS

James, IW, Linkers for solid phase organic synthesis, Tetrahedron, 55 4855-4946 (1999) USA.

Morphy, JR et al, A novel linker strategy for solid-phase synthesis, Tetrahedron Letters 37 3209-3212 (1996) USA.

Beyer, M et al, A novel glass slide-based peptide array support with high functionality resisting non-specific protein adsorption, Biomaterials, 27 3505-3514 (2006) USA.

Fernandez-Escamilla et al, Related Prediction of sequence-dependent and mutational effects on the aggregation of peptides and proteins, Nat Biotechnol 22 1302-1306 (2004) UK.

Lesaicherre, ML et al, Developing site-specific immobilization strategies of peptides in a microarray, Bioorg Med Chem Lett 12 2079-2083 (2002) USA.

Uttamchandani, M et al, Combinatorial peptide microarrays for the rapid determination of kinase specificity, Bioorg Med Chem Lett 13 2997-3000 (2003) USA.

Lesaicherre, ML et al, Antibody-based fluorescence detection of kinase activity on a peptide array, Bioorg Med Chem Lett 12 2085-2088 (2002) USA.

Fodor, Spa et al, Light-directed, spatially addressable parallel chemical synthesis, Science 251 767-773 (1991) USA.

Schena, M et al, Quantitative Monitoring of Gene Expression Patterns with a Complementary DNA Microarray, Science 270 467-470 (1995) USA.

Macbeath, G et al, Printing Small Molecules as Microarrays and Detection Protein-Ligand Interactions en Masse, J Am Chem Soc 121 7967-7968 (1999) USA.

Macbeath, G and Schreiber SL, Printing proteins as microarrays for high-throughput function determination, Science 289 1760-1763 (2000) USA.

Chen, Gyj et al, Array-based technologies and their applications in proteomics, Curr Top Med Chem 3 705-724 (2003) USA.

Panicker, RC et al, Advanced analytical tools in proteomics, Anal Chim Acta 556 69-79 (2006), Netherlands.

Uttamchandani, M et al, Protein and small molecule microarrays: powerful tools for high-throughput proteomics, Mol BioSyst 2 58-68 (2006) USA.

Joos, TO et al, A microarray enzyme-linked immunosorbent assay for autoimmune diagnostics, Electrophoresis 21 2641-2650 (2000) USA.

Ge, H, Upa, A universal protein array system for quantitative detection of protein-protein, protein-DNA, protein-RNA and protein ligand interactions, Nucleic Acids Res 28 e3 (2000) USA.

Vijayendran, RA and Leckband DE A quantitative assessment of heterogeneity for suface-immobilized proteins, Anal Chem 73 471-480 (2001) USA.

Lesaicherre, ML et al, Intein-mediated biotinylation of proteins and its application in a protein microarray, J Am Chem Soc 124 8768-8769 (2002) USA.

Lue, Ryp et al, Versatile protein biotinylation strategies for potential high-throughput proteomics, J Am Chem Soc 126 1055-1062 (2004) USA.

Hodneland, et al, Selective immobilization of proteins to self-assembled monolayers presenting active site-directed capture ligands, PNAS 99 5048-5052 (2002) USA.

Kindermann, M et al, Covalent and selective immobilization of fusion proteins, J Am Chem Soc 125 7810-7811 (2003) USA.

Yin, J et al, Labeling proteins with small molecules by site-specific posttranslational modification, J Am Chem Soc 126 7754-7755 (2004) USA.

Tan, LP et al, Expanding the scope of site-specific protein biotinylation strategies using small molecules, Bioorg Med Chem Lett 14 5735-5738 (2004) USA.

Tan, LP et al, Improving the intein-mediated, site-specific protein biotinylation strategies both in vitro and in vivo, Bioorg Med Chem Lett 14 6067-6070 (2004) USA.

Girish, A et al, Site-specific immobilization of proteins in a microarray using intein-mediated protein splicing, Bioorg Med Chem Lett 15 2447-2451 (2005) USA.

Zhang, K et al, Artificial polypeptide scaffold for protein immobilization, J Am Chem Soc 127 10136-10137 (2005) USA.

Watzke et al, Angew Chem Int Ed 45 1408 (2006) Germany.

Kwon, Y et al, Agnew Chem Intl Ed 45 1726 (2006) Germany.

Frank, R, Spot-synthesis: an easy technique for the positionally addressable, parallel chemical synthesis on a membrane support, Tetrahedron 48 9217-9232 (1992) USA.

Falsey, JR et al, Peptide and small molecule microarray for high throughput cell adhesion and functional assays, Bioconj Chem 12 346-53 (2001) USA.

Houseman, BT et al, Peptide chips for the quantitative evaluation of protein kinase activity, Nat Biotechnol 20 270-274 (2002) USA.

Houseman, BT et al, Maleimide-Functionalized Self-Assembled Monolayers for the Preparation of Peptide and Carbohydrate Biochips Langmuir 19 1522-1531 (2003) USA.

Pellois, JP et al, Peptide synthesis based on t-Boc chemistry and solution photogenerated acids, J Comb Chem 2 355-360 (2000) USA.

Leproust, E et al, Digital light-directed synthesis. A microarray platform that permits rapid reaction optimization on a combinatorial basis, J Comb Chem 2 349-354 (2000) USA.

Wenschuh, H et al, Coherent membrane supports for parallel microsynthesis and screening of bioactive peptides, Biopolymers 55 188-206 (2000) USA.

Reineke, U et al, Antigen sequence- and library based mapping of linear and discontinuous protein-protein-interaction sites by spot synthesis, Curr Top Microbiol Immunol 243 23-36 (1999) USA.

Thomas, DA et al, A broad-spectrum fluorescence based peptide library for the rapid identification of protease substrates, Proteomics 6 2112-2120, (2006) USA.

Ercole, F et al, A combinatorial approach in designing hydrophilic surfaces for solid-phase peptide synthesis, J Appl Polym Sci 89 3371-3378 (2003) USA.

Bui, CT et al, Acetophenone-based linker for solid-phase peptide synthesis, J Pept Sci, 6 49-56 (2000) USA.

Bui, CT et al, Improving the performance of an acid-labile 4-hydroxymethylphenoxyacetic acid (HMP) linker on resin and SynPhase grafted solid-supports, J Pept Sci 6 534-538, (2000) USA.

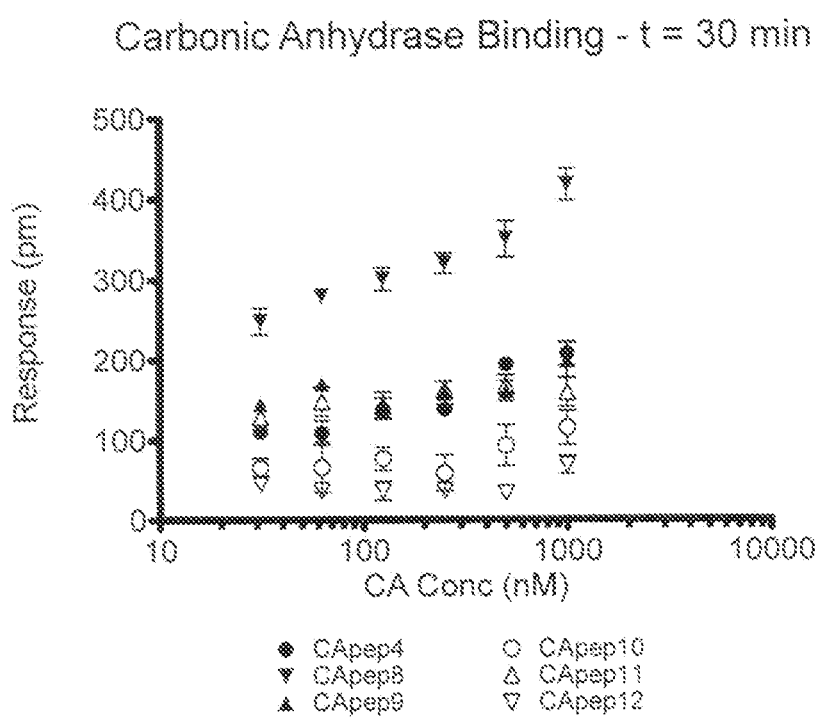

A					B

Peptides that show inhibition on the enzyme activity

Peptides that show enhancement on the enzyme activity

IMMOBILIZING AN ENTITY IN A DESIRED ORIENTATION ON A SUPPORT MATERIAL

PRIORITY CLAIM

This application claims priority to the U.S. provisional application 60/973,974, which was filed Sep. 20, 2007, the contents of which are incorporated herein in their entirety.

STATEMENT OF GOVERNMENTAL INTEREST

This invention was made without Government support.

FIELD OF THE INVENTION

The present invention relates to the identification and selection of attachment molecules that attach/immobilize an entity having a detectable activity or property on a support in an orientation that provides a detectable activity or property, and to surfaces made of the attachment molecules.

BACKGROUND OF THE INVENTION

The past approaches described in this section could be pursued, but are not necessarily approaches that have been previously conceived or pursued. Therefore, unless otherwise indicated herein, the approaches described in this section are not to be considered prior art to the claims in this application merely due to the presence of these approaches in this background section.

Solid phase and microarray analysis involve the attachment of capture molecules, herein referred to as "entities" such as antibodies or enzymes to a support/solid matrix in a way that preserves the activity of the entity and its ability to bind to a specific target molecule. In an array, entities specific for particular targets are attached to specific identifiable locations on the matrix. After exposure to a sample suspected of containing one or more target analytes, the matrix is analyzed to determine if substances in the sample bind to the capture molecules at one or more locations on the array.

Two-dimensional microarrays have proven useful for a wide range of applications, such as in protein research. However, proteins are more difficult to attach to a solid matrix and far more complex than oligonucleotides. Thus, techniques for immobilizing a protein (antibody, enzyme, and receptor) on a microarray often require modifications compared to the more simple nucleic acid microarrays. (See, e.g., Constans, A., "The Chipping News", The Scientist 2002.)

Many clinical diagnostic devices have been built around solid phase and microarray platforms incorporating an appropriate solid matrix to which a plurality of entities are permanently affixed to the matrix. Typically entities are attached to the surface of the solid matrix using covalent, electrostatic or hydrophobic bonding so that the entities/capture molecules remain attached to the surface during sample analysis. Target molecules that bind to the entity may be detected in a variety of ways, most commonly by attaching fluorophore tags to the target molecules. Scanners, CCD cameras or similar detectors may be used to determine the location and signal intensity of fluorescent tags bound to matrix arrays.

The amount of entity that can be affixed on a surface depends on the surface chemistry and on the nature and size of the capture molecule/entity. If insufficient amounts of entity are affixed to the surface, the resulting signal will be too weak to detect even if the entity captures or binds a tagged target molecule. Further, binding to the surface must also preserve the functional activity or property of interest of the entity.

Methods used for immobilizing entities on a support include direct covalent or electrostatic linkage of the entity to polystyrene, glass or other material; biotinylating the entity and binding it to streptavidin bound to the surface; and other similar methods. Such methods can lead to undesirable alterations of the activity or properties of the entity, which could lead to problems ranging from reduced sensitivity of an assay to inaccurate results.

Antibody based assays like Elisas and radioimmunoassay (RIAs) use antibodies or antibody fragments as attachment molecules to bind to a target. However, antibodies are costly and time-consuming to produce and screen. Even antibody fragments produced by phage display technology require a number of time consuming, iterative operations to produce a sufficient number of antibodies of a sufficient variety to test the ability of any one of them to capture an entity in a desired orientation. In addition, antibodies are large proteins, with only one or two antigen binding sites per antibody monomer. As a result, such molecules have a very high molecular weight per binding site, which potentially reduces the sensitivity of the assay.

Therefore, there is a need for a surface with a high number of binding sites per unit mass to bind and orient entities in their native form or in a desired conformation or orientation on a support material with a simple, rapid, and uniform method of producing the surface.

DEFINITIONS

As used herein "entity" means any molecule or aggregate of molecules or fragment or variant thereof, cell, cell fragment or organelle that is immobilized on the surface of a support by binding to one or more attachment molecules. In a preferred embodiment the entity has an affinity for, binds to or reacts with a target. Where the molecule is biologically active, the target includes a biologically active fragment or variant thereof.

As used herein "target" means any molecule or aggregate of molecules or fragment or variant thereof, cell, cell fragment or organelle that binds to or reacts with an entity. The target may bind to the entity either before or after the entity is immobilized on the surface of the support; alternatively the entity and target may bind during the immobilization process. Where the molecule is biologically active, the target includes a biologically active fragment or variant thereof.

"Entities" and "targets" include, but are not limited to, any protein such as enzyme, ribozyme, receptor, transfection factor, polyclonal antibodies, monoclonal antibodies of the A, D, E, G or M classes, free light or heavy chain of immunoglobulin antibody fragment, FAb fragment, humanized antibodies, single-chain antibodies, chimeric antibodies, variable region, hypervariable region, or constant region of the immunoglobulin, histone, nucleoprotein, lipoprotein, glycoprotein, peptoid, peptidomimetic, mammalian blood or plasma protein constituent (including albumen, thyroxin binding globulin, haptoglobin, ceruloplasmin, myoglobin, fibrinogen, plasminogen), complement factor, blood clotting factor, peptide, peptidoglycan, lipid, fatty acid, triglyceride, phospholipids, small molecules (organic or inorganic), and protein hormone, growth factor, allergen, antigen, substrate, metabolite, cofactor, inhibitor, pharmaceutical, cytokine, carbohydrate, polysaccharide, oligonucleotide, polynucleotide, nucleic acid, and aptamer, nutrient, toxin, poison, explosive, pesticide, chemical warfare agent, biowarfare agent, biohazardous agent, infectious agent, prion, radioisotope, vitamin, heterocyclic aromatic compound, carcinogen, mutagen, narcotic, amphetamine, barbiturate, hallucinogen, waste product, contaminant, heavy metal or any other molecule or atom, without limitation as to size. Entities and targets can be a virus, bacterium, spore, mold, yeast, algae, amoebae, protozoan, dinoflagellate, unicellular organism, pathogen, cell, organelle, or cell fragment.

As used herein "activity" and "property" mean any activity or property of an entity or of a target or of the target/entity complex that can be detected directly or indirectly. In some embodiments the activity or property of an entity undergoes a detectable change either through the process of binding the surface of the support, or by binding to or interacting with one or more target molecules. Likewise the activity or property of a target can be changed by binding to an entity. In a simple example, an activity is the ability of an antigen to recognize and bind to an antibody or visa versa. In another example the activity is the ability of an enzyme to bind to and hydrolyze a target substrate. In other examples the conformation of an entity (a property) is changed by binding of the entity to the substrate or to the target. In examples where the entity is a cell, the activity may be the ability of the cell to undergo a physiological response or to interact with a target.

"Active region" means any region of an entity that when interfered with changes a property or activity of the entity in a way that can be detected. Active region includes the active site on a molecule such as the part of a protein that must be maintained in a specific conformation if the protein is to be functional, for example, the substrate-binding site on an enzyme, or the antigen-binding site on an antibody, or a functional moiety on the entity that participates in a chemical reaction with one or more other molecules. The active region includes both a specific well-defined site and a generalized locus, the boundaries of which are approximate, not necessarily known or determinable, and that may vary according to the prevailing conditions. The active region can include more than one specific site or region the accessibility and/or conformation of which affect the activity or a property of the entity, such as its ability to bind a target or participate in a reaction of interest. If an entity has more than one active region, the attachment molecule is selected so that the active region(s) of interest are open i.e. oriented to permit the property or activity to occur and be detected. Active regions on entities that are cells include cell surface receptors where binding of a target to the receptor initiates a physiological response; ion channels that can generate an action potential or current under appropriate conditions; cell surface antigens such as cancer cell-specific antigens that are recognized by bound antibodies (entities) thereby selectively removing the cancer cell from a biological sample; and so on.

As used herein "protein" or "polypeptide" means any chain of amino acids, regardless of length or post-translational modification (e.g., glycosylation or phosphorylation). "Peptide variants" means polypeptides that may contain one or more amino acid substitutions, additions, deletions and/or insertions including non-naturally occurring amino acids. Such modifications may be readily introduced using standard mutagenesis techniques, such as oligonucleotide directed site-specific mutagenesis as taught, for example, by Adelman et al. (DNA, 2:183, 1983). Variants of the attachment peptides described herein come within the meaning of attachment peptides. Peptide variants also include peptides to which side chains have been added.

"Attachment molecule" means any molecule which, when bound to a support material forms a surface on the support that will bind an entity thereby immobilizing the entity on the support in an orientation and/or state in which the entity exhibits a detectable activity and/or property of interest. Attachment molecules include but are not limited to any protein, polypeptides, nucleic acids, aptamers, polymers, carbohydrates, polysaccharides, and glycoproteins having any type of side chain, primary, secondary or tertiary structure or branching topology. The preferred embodiment is a peptide, herein referred to as an "attachment peptide."

An "attachment peptide" means a peptide or peptide variant that is an attachment molecule. In a preferred embodiment the peptide is from about 8-20 amino acids long. In another preferred embodiment the peptide is attached to the support (or to a functionalized surface on the support) via a cysteine residue at the C-terminus of the peptide. Routine experimentation will determine the optimum length, which can be greater than 20 residues, and in some cases may be less than 8 residues. The attachment peptides bind the entity immobilizing it on the surface of the support in an orientation that either optimizes or minimizes an activity or property of interest, for example the availability of the binding site. By optimize is meant a level of activity that is higher than it would be if the entities were bound to the surface of the support in random orientations. By minimize it is meant a level of activity that is lower than it would be if the entities were bound to the surface of the support in random orientations.

As used herein, "immobilization" of an entity on a support by one or more attachment molecules means that the entity is bound to the surface of the support for a time and under the conditions that permit the activity or property to be detected. Immobilization has it usual meaning in the art of assays using support materials to which entities are bound.

"Substantially identical" means that the amino acid sequence of the attachment peptides are about 80% identical, preferably 90%, most preferably about 95% identical. In the preferred embodiment, identical attachment peptides are bound to the support material to create the desired surface, however, there may be some fragments or impurities that make the peptide coating less than completely identical.

"Binding" as used herein includes covalent or non-covalent interactions, such as hydrogen bonds, salt bridges, and Van der Waals interactions, electrostatic bonds, ionic bonds, hydrophobic bonding, and adsorption of a molecule to a surface.

"Functionalized surface" as used herein means a surface of a support that has a particular chemical property (i.e. a surface chemistry). Functionalized surfaces include supports coated with a polymer, or a polymer bound to a linker, or a polymer bound to a linker bound to an attachment molecule, and surfaces treated chemically or by vapor deposition. Functionalized supports include exposing one or more chemical moieties functional groups, or molecular structures.

The terms "detection" and "detecting" are used herein to refer to any assay or measurement or procedure that indicates the presence of one or more specific targets in a sample, or that indicates the presence and/or the level of a particular activity or property (or change therein) of the entity or target, or that indicates the occurrence of a particular activity such as a chemical reaction in which either the entity or target or both participate.

Aspects of the invention are described below in the drawings and detailed description of the invention. Unless specifically noted, it is intended that the words and phrases in the specification and the claims be given their plain, ordinary, and accustomed meaning to those of ordinary skill in the art.

BRIEF DESCRIPTION OF THE DRAWINGS

The present invention is illustrated by way of example, and not by way of limitation, in the figures of the accompanying drawings in which like reference numerals refer to similar elements.

Figure 1:
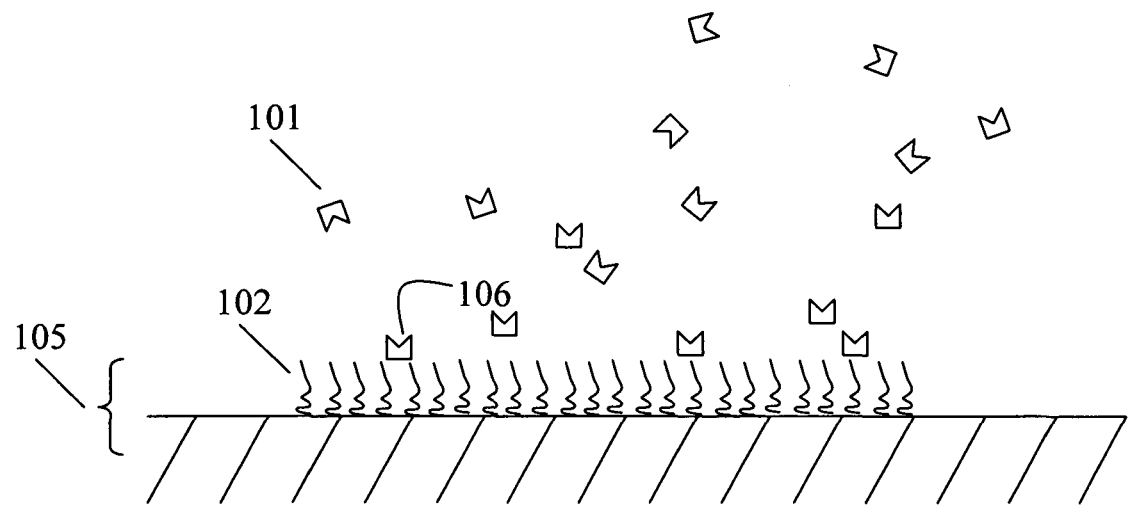
FIG. 1 depicts the binding of an entity (101) to a surface (105) coated with attachment molecules (102). The active region of the entity is (106).

Elements and facts in the figures are illustrated for simplicity and have not necessarily been rendered according to any particular sequence or embodiment.

DETAILED DESCRIPTION

In the following description, for the purposes of explanation, numerous specific details are set forth to provide a thorough understanding of the present invention. It will be apparent, however, to one skilled in the art that the present invention may be practiced without these specific details. In other instances, well-known structures and devices are shown in block diagram form to avoid unnecessarily obscuring the present invention.

Certain embodiments of the invention are directed to a surface for immobilizing an entity having an active region or a property of interest, made of a plurality of substantially identical attachment molecules bound to a support material to create a surface that is capable of immobilizing an entity in a desired orientation, for example an orientation that optimizes accessibility of the active region for binding to or otherwise interacting with a target or optimizes the property. In other embodiments the desired orientation is one that reduces activity, for example, by blocking the active site. In other embodiments binding of the entity to the surface of the support alters the conformation of the entity thereby changing its activity or other property. The support surface made of attachment molecules, preferably peptides, is one type of functionalized surface. The surfaces of the present invention can be used for Elisas and RIAs, or for any assay, procedure, reaction or measurement that can use an immobilized entity. The new surfaces have many other uses discussed in more detail below. In some embodiments a mixture of different attachment molecules can be used to create a surface that binds and immobilizes the entity in a desired orientation.

In certain other embodiments different attachment molecules specific for different entities are organized in a microarray on the surface of a support material, thereby immobilizing the respective different entities at discrete locations on the support to permit, for example, high throughput screening assays for targets that bind to the different entities.

Certain other embodiments are directed to methods for identifying attachment molecules that bind a particular known entity thereby immobilizing it on the support in a desired orientation and/or state that optimizes the particular activity or property of interest. Example 1 describes selecting attachment peptides that form a surface on a support material that selectively binds and immobilizes the enzyme carbonic anhydrase on the support in an orientation that optimizes the ability of the enzyme to bind the known inhibitor dansylamide. Carbonic anhydrase so bound can be used in assays to detect the presence of the inhibitor in a sample, or to screen for other targets that inhibit or activate the enzyme. Alternatively, the enzyme immobilized on the surface of the support may be used to cleave a known substrate.

In one embodiment, the attachment peptide (102) is bound to the support material (105) to create a surface that binds a known entity; the entity (101) is bound to the attachment peptide in an orientation that leaves the active site (106) on the entity open to bind to or interact with the target (101). See FIG. 1. The attachment molecules can be optionally cross-linked to the support material. In some embodiments the attachment peptides have a greater affinity for the entity than for other species that may be present in a sample. In some embodiments the entity is cross-linked to the attachment molecule. The cross-linking can be accomplished using any method known in the art. In one example cross-linking is accomplished where a group such as an N-terminal Gly-Gly-His sequence initiates cross-linking in the presence of a per-acid. In some embodiments the attachment molecules are cross linked to a functionalized surface of polymer such as polylysine coated on the support.

Figure 2:
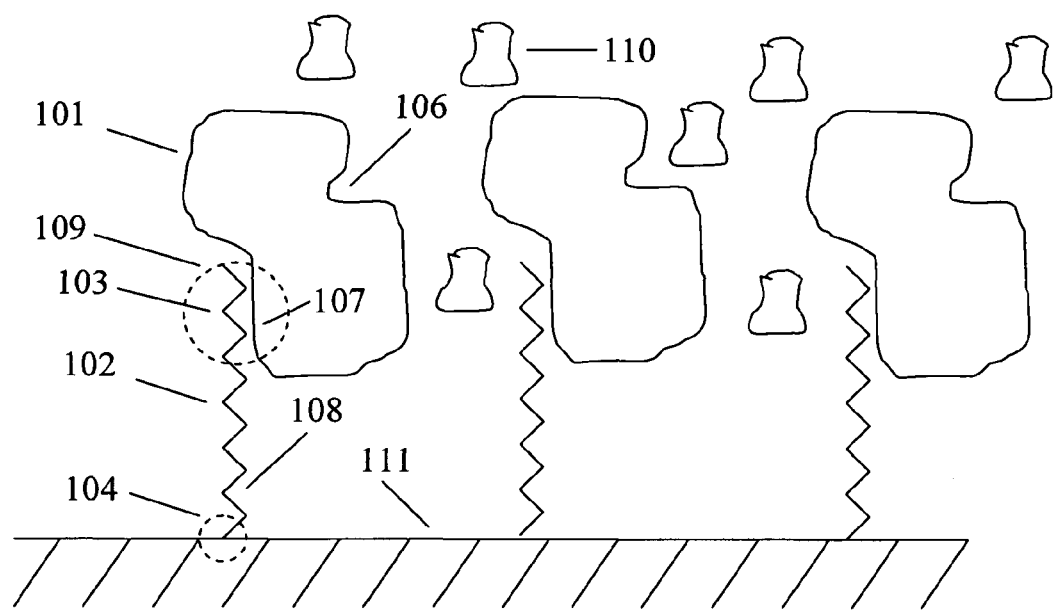
FIG. 2 depicts an example of a target (110), capable of binding to an entity (101) via an active site (106) on the entity. The entity (101) is bound via attachment site (107) on the entity to attachment molecule (102) via entity binding site (103) on the molecule. In this example the attachment molecule (102) is connected to the surface (111) of support (105) via linker (104).

In another embodiment, illustrated in FIG. 2, the target (110) binds entity (101) via active site (106) on the entity. The entity (101) is bound via attachment site (107) on the entity to attachment peptide (102) at entity binding site (103) on the peptide. In this example the attachment peptide (102) is bound to the surface (111) of the support material via a linker (104). In a preferred embodiment the attachment peptides forming a surface on the support (or at a discrete locus on the support) are all the same (or substantially identical) for binding a given entity. However, a mixture of different attachment peptides can be used to immobilize a single entity as long as they bind the entity to the support material with the desired orientation optimizing (or minimizing as may be the case) the property or activity of interest. In another preferred embodiment the support has a microarray of different attachment peptides located at different distinct locations on the support, where each different attachment peptide is specific for binding a particular entity.

Figure 4:
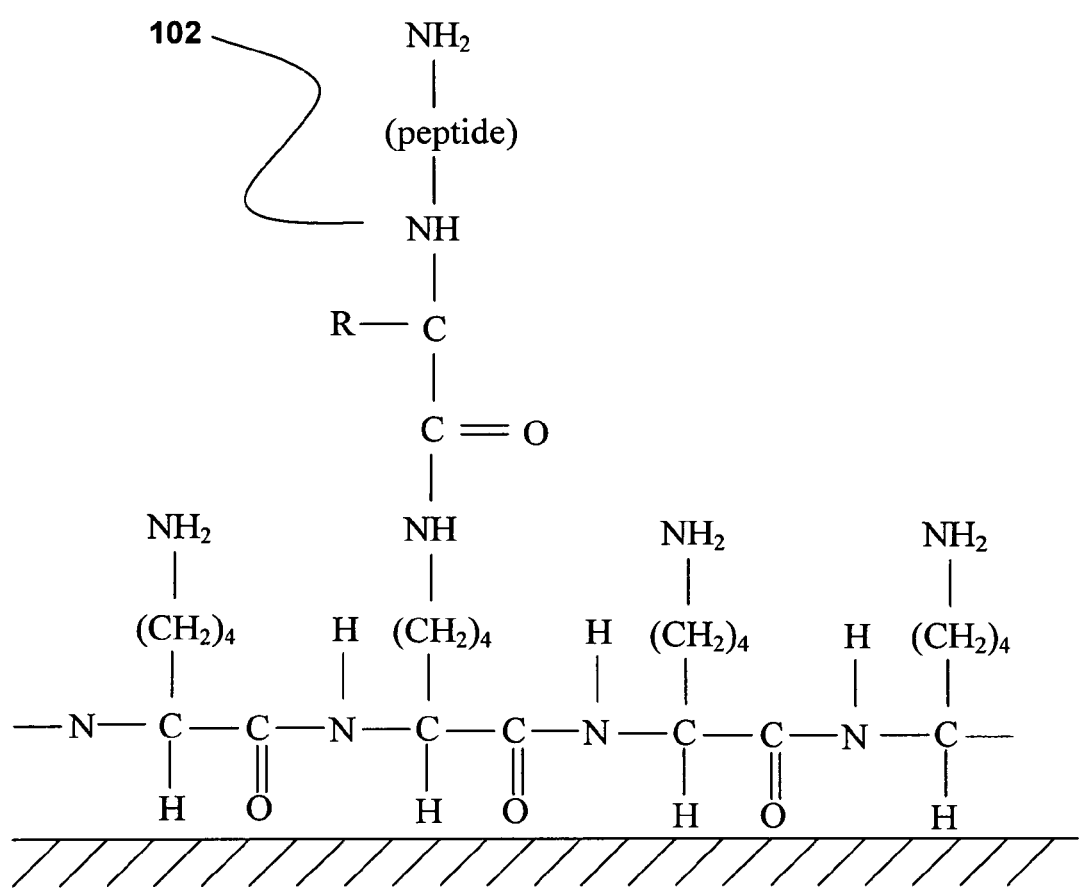
FIG. 4 depicts an example of an attachment peptides (102) bound to the support (111) via an amide bond (113) to a poly-lysine coating (112) that is non-covalently bound to the surface of the support (111) material.
Figure 5:
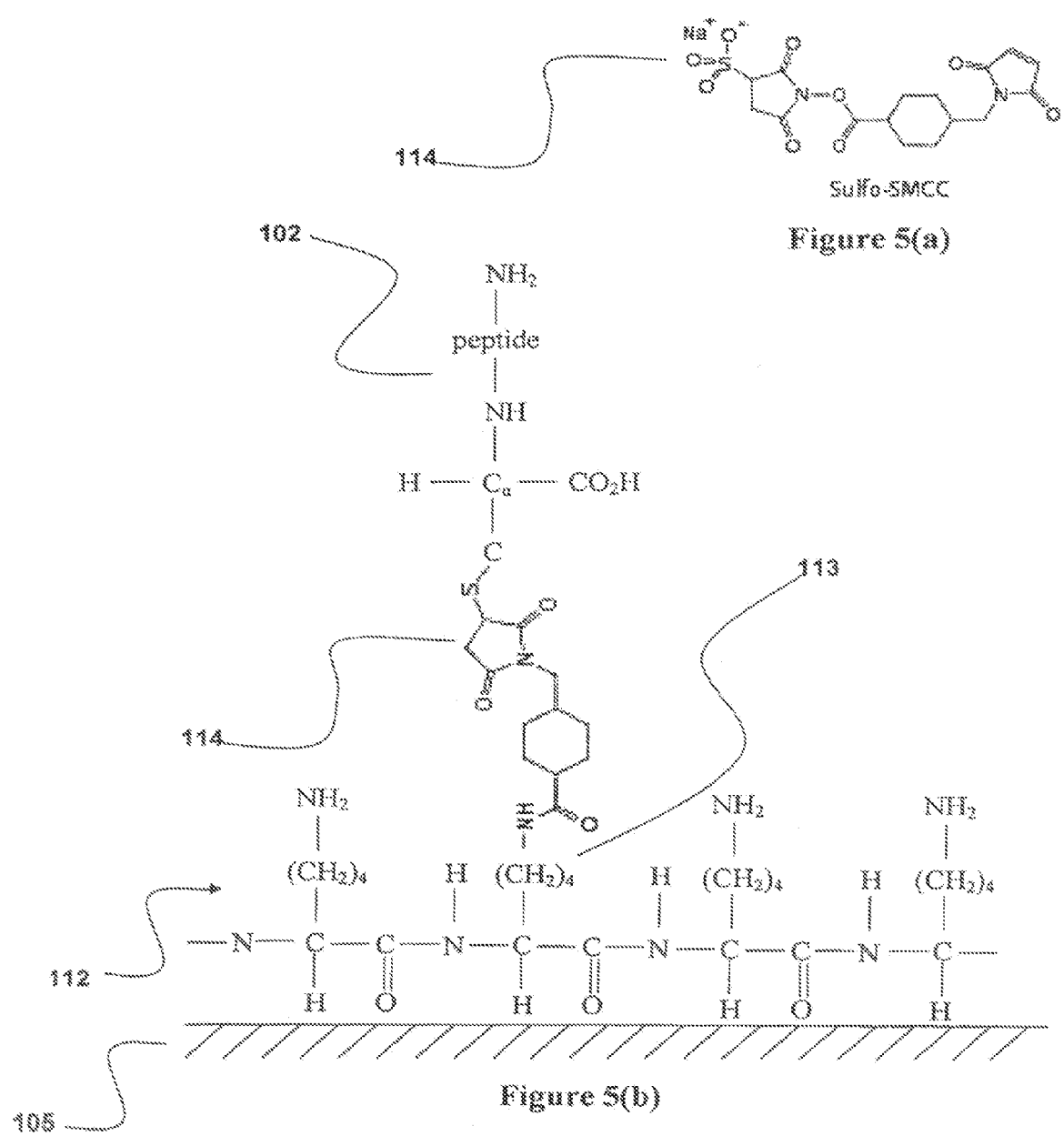
FIG. 5(a) depicts a maleimide molecule (114)
FIG. 5(b) depicts an example of an attachment peptide (102) bound via a thiol bond to a maleimide linker molecule (114), which linker is bound via an amide bond to a polylysine coating (112) on support (111).

In one embodiment, attachment peptides are attached to a poly-lysine coated surface on a support through the C terminus of the peptide that forms an amide bond to the side-chain amine of a lysine monomer of the poly-lysine surface coating. See FIG. 4. In another embodiment the C-terminal cysteine of the polypeptide is attached via a thiol linkage to a maleimide (sulfo-SMCC, sulfosuccinimidyl 4-[N-maleimidomethyl] cyclohexane-1-carboxylate, see FIG. 5(a)), which is covalently bonded to the side-chain amine of a lysine monomer of the poly-lysine surface coating, as shown in FIG. 5. The attachment molecule/peptide may also be confined to a region on the surface of the support by trapping it within a matrix such as a hydrogel, held by a linker (e.g. Polyethylene glycol, PEG) of any length, or using any other method known in the art. Example 2 describes a case where the substrate for a bound enzyme entity is applied in a hydrogel to localize the reaction and reaction products.

In a preferred embodiment a polymer or other coating is deposited on the surface of the support to increase either the number of attachment molecules that bind to the support or the strength of the bond of the attachment molecules to the support, or both. Such a coated surface is a type of functionalized surface. In a preferred embodiment the coating is a polymer such as polylysine or polycysteine. Any coating known in the art that provides a functionalized surface to which the attachment peptides will bind either directly or via a linker molecule can be used.

Characteristics of the Attachment Molecules/Attachment Peptides

As defined above, attachment molecules include any molecule that, when bound to a support, creates a surface that will bind an entity thereby immobilizing the entity in proximity to the surface in an orientation and/or state in which the entity exhibits a desired activity or property. Attachment molecules include polypeptides, nucleic acids, aptamers, polymers, carbohydrates, polysaccharides, glycoproteins having any type of side chain, primary, secondary or tertiary structure or branching topology. In a preferred embodiment the attachment molecule is a peptide.

Factors to consider in selecting an attachment molecule include (1) the strength and/or stability of (1) the bond between the attachment molecule and the support, (2) the strength and or stability of the bond of the entity to the attachment molecule; (3) the activity/property of the entity when it is immobilized on the support; and (4) the tendency of the entity, attachment peptide, support material, or combination thereof to interact in undesired ways with each other or with any target or other compound that may be present under the conditions used. Any such criteria may be evaluated individually or in any combination or by any metric deemed useful to choose the best attachment molecule/support/entity combination.

In the context of the present invention binding between a target and an entity, or between an entity and an attachment molecule/attachment peptide, or between an attachment molecule/attachment peptide and a surface (functionalized or not functionalized) of a support, results in a sufficiently stable complex so as to permit detection of the target:entity complex bound to the support. However, in some embodiments the attachment peptide is selected so that the entity detaches from the support upon binding to or reacting with a target.

The attachment molecule may be applied to a support or a functionalized surface on the support (such as a polymer coating on a support) in its final form. Alternatively, the attachment peptide (or other type of attachment molecule) may be assembled on the support in components that are mixed, reacted, or otherwise combined during or after application. Alternatively an attachment molecule may be synthesized in whole or in part in situ.

In a preferred embodiment the attachment molecules are peptides that are at least three amino acids long, preferably 8-20 amino acids long. In another preferred embodiment the C-terminus of the attachment peptide is a cysteine residue through which the peptide attaches to the support or a functionalized surface on the support. In another embodiment the last three C-terminal amino acids are glycine-serine-cysteine. In other embodiments the peptides are synthesized according to sequences determined by a pseudorandom computational process in which each of the 20 naturally occurring amino acids except cysteine had an equal probability of being represented at each position. Routine experimentation will determine the optimum length, which is not limited to and can exceed 20 residues and can be less than 8 amino acids long.

Screening for Attachment Molecules that Bind a Particular Known Entity

A preferred embodiment of the invention is directed to a high throughput screening method to identify one or more attachment molecules for immobilizing the known entity of interest on a support in an orientation or state that preserves, increases or otherwise optimizes the desired activity or property of the entity. One embodiment is directed to a method for identifying one or more such attachment molecules for immobilizing an entity having an active region to a surface of a support material in an orientation that optimizes the availability of the active region for binding to a known target, by:

providing a support material having a surface comprising a plurality of different molecules bound at respective different locations on the surface in a microarray;

contacting the plurality of molecules with the entity under conditions that permit the entity to bind to the molecules;

contacting the entity with the known target under conditions that permit the entity to bind to the target, determining whether the entity binds the target at each respective different location; and selecting the molecule or molecules at those locations where the entity binds the target.

In another embodiment the entity is reacted or incubated with the target and the entity/target complex is then contacted with the surface of the support to determine which of the attachment molecules on the surface bind the complex. Additional binding assays can be performed to identify which of the selected attachment molecules best optimizes (or minimizes or otherwise affects) the desired activity, property, specificity or affinity of the entity for the target. These attachment molecules/peptides are then selected. Some examples are described in detail in the Examples.

In some embodiments the attachment molecule is free in solution and is contacted with the entity to form an attachment molecule/entity complex that is then bound to the support. In other embodiments the attachment molecule is free in solution and contacted with both the entity and the target, thereby permitting formation of an attachment molecule/entity/target complex that is then bound to the support. A person of skill in the art can manipulate the steps to select attachment molecule in various ways.

The activity or other property of interest can be any detectable activity or property, such as enzymatic cleavage of a substrate, catalysis of a reaction, antibody-antigen binding, receptor-antagonist/agonist binding, ion channel conductivity, etc., which may be detected in any manner known in the art. In certain embodiments binding assays or other measurements or analysis or quantitation of the activity/property being detected can be performed in situ on the support.

Figure 3:
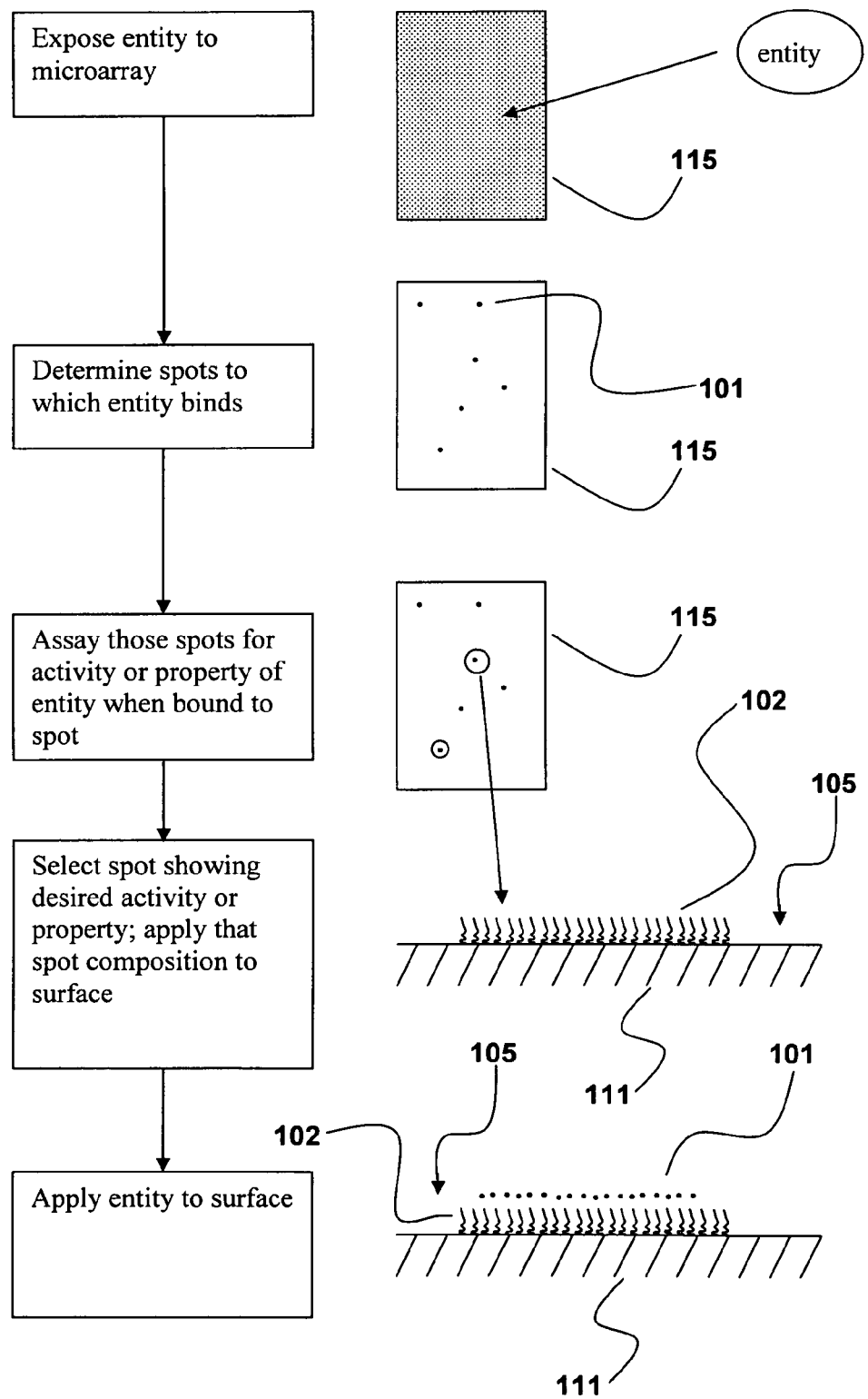
FIG. 3 depicts an example of a screening process that identifies attachment molecules (102) that bind a particular entity (101) using a microarray (115) of different attachment molecules (102) located at distinct locations on the array. The entity (101) binds the attachment molecule (102) that is attached to the surface of support (111).

FIG. 3 illustrates a generalized scheme for identifying attachment peptides for a known entity. One embodiment for selecting one or more attachment peptides with the desired preferential affinity for a particular enzyme entity has the steps of: (a) exposing the entity, such as an enzyme to a robotically spotted polypeptide microarray having 4,000 to 10,000 distinct spots each of which has a distinct known polypeptide composition; (b) identifying the polypeptide composition of the spots to which the enzyme binds; (c) evaluating the activity of the enzyme when bound to surfaces comprising each of the identified polypeptide compositions; and (d) selecting the polypeptide composition upon which the enzyme has optimal activity for use as the attachment peptide.

Binding of the entity to the various attachment molecules or binding of the target to the entity may be determined by any of the many methods known to persons having ordinary skill in the art, such as direct fluorescent labeling or use of a fluorescently labeled antibody, radioisotope labeling and the like. Evaluation of the activity or property of the entity when bound to the support may be accomplished by separate assays each employing a single attachment molecule species, or by assaying activity of the entity in situ on the microarray. In a preferred embodiment where the entity is an enzyme, an in situ assay is performed by contacting the microarray onto which the enzyme has been bound with the enzyme's substrate and a suitable reporter in a non-reactive viscous medium such as a hydrogel film to limit diffusion and localize the reaction site for easy detection. See Example 2 describing selection of an attachment peptide that immobilizes the entity beta-galactosidase in an orientation on the support that preserves its ability to bind to and hydrolyze its substrate FDG, which is applied to the support in a hydrogel.

Selection may also be accomplished by screening a plurality of candidate attachment molecule distributed in different wells of well plates or on other suitable surfaces or vessels. It is preferable to test the binding of attachment molecule to the entity on a support material that is similar in material respects (if not identical) to the support material upon which the attachment molecule will ultimately be used.

In various embodiments the screening method includes (a) providing a plurality of individually evaluable support loci, each support locus having a candidate attachment molecule composition; (b) contacting each of the support loci with an entity; (c) identifying at least one of the support loci having an attachment molecule composition capable of immobilizing the entity; (d) evaluating an activity or property of the entity when immobilized to at least one of the identified support loci; (e) identifying at least one of the identified support loci at which the evaluated activity or property corresponds to desired criteria; and (f) selecting at least one attachment molecule composition corresponding to a locus at which the activity or property corresponds to desired criteria.

In some embodiments the screening method includes (a) providing a plurality candidate attachment molecules; (b) contacting each of the candidate attachment molecules with an entity; (c) identifying at least one of the candidate attachment molecules capable of binding to the entity; (d) evaluating an activity or property of the entity when bound to the identified candidate attachment molecules; and (e) identifying at least one of the identified candidate attachment molecules whereby the evaluated activity or property of the entity when bound thereto corresponds to desired criteria.

All or any part of the screening methods disclosed herein may be performed using any operable technique and/or screening modality, including microarrays on which candidate attachment molecules are spotted, synthesized in situ, or otherwise exposed; bead or resin based screening methods; screening methods in which candidate attachment molecules are present in the wells of a well plate; and methods in which candidate attachment molecules are present on a substrate suitable for a particular evaluation technology such as, by way of non-limiting examples, surface plasmon resonance, Corning Epic technology, and mass spectrometry. In some embodiments all or part of the disclosed screening methods may be performed using solution phase techniques; by way of non-limiting example, the affinity of an attachment molecule for an entity, and/or an activity or property of an entity as affected by the presence of an attachment molecule bound thereto, may be evaluated in solution phase in some embodiments. Many screening modalities are known in the art and the disclosures hereof extend to any operable screening modalities and/or combinations thereof.

Selecting Entities and Targets

Because both targets and entities can be any molecule, aggregate of molecules or even a cell or organelle, we have defined these components in terms of their position on the surface of the support and their relationship to each other. An entity is a molecule that binds to the attachment molecules that make up the surface of the support either directly or through a linker attached to a polymer coating. A target is any molecule that binds to the entity. In one embodiment the entity is a receptor, and the target a potential new agonist or antagonist screened in a high throughput assay. In another embodiment a known receptor antagonist is the entity and the receptor is the target. Likewise the positions of antigen/antibodies may be either entity/target or target/entity. In some embodiments the entities are antibodies that recognize a cancer antigen on the surface of a cancer cell, and the target is the cancer cell, or visa versa.

In some embodiments using the new surfaces of the present invention functionalized by coating with highly selective attachment molecules, an entity is bound to the surface of the support in an orientation that optimizes the availability of the active site for binding to the target. Diagnostic uses of Elisas and solid phase RIAs are well known, and can be optimized using the technology disclosed herein. If an entity has more than one active region, the attachment molecule can be chosen to selectively expose the active region of interest while blocking the other active regions. For example, binding of the entity to the attachment molecule may induce a conformation change in the entity that optimizes availability of the active region of interest while minimizing the availability of other active regions, thus optimally orienting the active site for binding to the target. Alternatively, in some cases it may be desirable to optimize availability of all of the active regions, for example, to eliminate targets that bind nonspecifically to more than one active region on the entity, thereby permitting selection of a target that has a significantly greater affinity for one site than any other.

Any molecule with a functional moiety that participates in a chemical reaction with one or more other molecules can be used as an entity. Thus the surfaces formed of attachment molecules can be used in a bioreactor, for example, to immobilize one or more key enzymes on a support in an orientation that improves the reaction rate. In certain embodiments, different attachment molecules that immobilize different respective entities are organized on the surface of a support to bind the different respective entities in a particular desired order or proximity that optimizes the rate of a series of sequential reactions involving the different entities. In other embodiments, one or more lipase enzymes in a reactor are bound on a support to expedite the enzymatic modification of oils or fats.

Other uses include providing a surface that immobilizes one or more molecules involved in or affecting the complement system in such a way as to prevent the initiation of a complement cascade. In another embodiment substances involved in or affecting coagulation may be bound to a support in a manner or order that minimizes coagulation. In some embodiments entities are immobilized to minimize their immunogenicity. The new surfaces can also be used in a drug delivery device that maintains a drug molecule in a desired orientation or state, perhaps selecting the support material so that it dissolves after a certain time such as when the drug has been exhausted or degraded. In some embodiments the surfaces are used for purification or separation applications in which the entity (or more than one entity) is immobilized on a surface of attachment molecules for chromatography or filtration in an orientation or state that optimizes the desired interaction of the entity with components (impurities, toxins or known targets) in the liquid or gas phase. For example, the immobilized entity may be a receptor that is immobilized on the solid phase of a chromatography column in an orientation or state that permits it to bind to a known ligand, pathogen or toxin in a biological sample thereby selectively removing the ligand, pathogen or toxin from the sample. In some applications the entities remain immobilized, making it unnecessary to remove the entities from the sample after the reaction occurs. In other embodiments the entity detaches from the support upon binding to a certain target molecule. This may be accomplished by choosing an attachment molecule to which the entity binds with a lower affinity than the entity has for the target.

An entity includes organelles and cells such as a cancer cell. In some embodiments an entity that selectively binds to a surface antigen on a particular cell type is immobilized on a surface, thereby facilitating the separation of the cells from a heterogeneous population. Examples include antibodies directed against a cancer antigen on the surface of a cancer cell, or a neuron-specific surface antigen on a neuron, or a bacterial surface antigen on a bacterium. Similarly, a cell can be immobilized in order to identify targets that bind to the cell, such as particular antibodies, cytokines, pharmaceuticals or antigens, etc. In other embodiments an entity is selected that cleaves a particular surface marker or other molecule or molecular complex from the surface of cells, with the advantage (as compared to application of the entity in solution phase) of avoiding contamination of the sample with free entity in solution.

In other embodiments it may be desirable to immobilize a cell on a support to study various properties of the cell, for example electrophysiological properties of a neuron, membrane barriers of endothelial cells that make up the blood brain barrier, and the like. Another embodiment is directed to immobilizing one type of cell near another type of cell to study the intercellular interactions. Such immobilization may be by patterning attachment molecules having preferential affinity for the respective cell types of interest, or having preferential affinity for entities that in turn have preferential affinity for the respective cell types of interest, in a desired layout.

In certain embodiments a property of the entity itself such as the light-scattering or absorbing properties of the entity, or its NMR spectrum is altered by binding to the attachment molecules.

Each entity (101) has at least one capture region (107) through which it binds to a capture region (103) on the attachment molecule/peptide (102). Attachment molecules/peptides typically bind to a protein entity such as an enzyme, via one or more noncovalent interactions, such as hydrogen bonds, salt bridges, hydrophobic interactions and Van der Waals interactions between various residues on the polypeptide and various residues accessible on the surface of the entity. In some embodiments binding is via covalent or other chemical bonds. In other embodiments, the entity is sufficiently immobilized and stably oriented by adsorption onto the surface formed by the attachment peptides bound to the support. It is not necessary that the extent or locations of capture regions of entities and/or attachment molecules, the nature of the interactions between entities and attachment molecules, the position and/or geometry of the immobilization of the entity, the number of capture regions, the number of attachment molecules interacting with each entity, or any other details of the interface between the attachment molecules and the entities be known or determined. In various embodiments such information is not known or determined, and attachment molecules are selected and/or evaluated on the basis of one or more desired activities and/or properties of the entities when bound. Attachment molecules that bind to the entity in an orientation and/or state that facilitates the desired activity and/or properties are simply selected from a plurality of candidate molecules based on achieving the desired result.

In some embodiments where a desired activity or property depends upon non-interference with an active region, the capture region (107) on the entity (101) is preferably distinct and physically removed from the active region(s) so that the active region is accessible to the target when the entity is bound to the support. The attachment molecule/peptide should have adequate affinity for the entity so that the entity is not easily dislodged or its orientation and state disrupted under the conditions used, taking into account any avidity, cooperativity, trapping, or other similar effects, and the interaction of the attachment molecule/peptide with the entity should preferably not adversely affect the activity or other property of interest of the entity. The elegance of the present method is in part the fact that one does not have to identify the locus on the entity to bind to the attachment molecule/peptide. A high throughput screen of attachment molecule/peptides will enable the user to select those that bind the entity in the desired orientation. An entity may have more than one capture region, and may interact with more than one moiety and/or more than one attachment molecule/peptide. The same attachment molecule/peptide may interact with an entity at a first capture region and with another identical entity molecule at a different capture region, as long as the desired activity or property is achieved when the entity is bound to the support.

Where it is important to optimize the activity being monitored, the affinity of the attachment molecule/peptide for a capture region on the entity should preferably exceed the affinity of the attachment molecule/peptide for the active region on the entity. Similarly, the affinity of the attachment molecule/peptide for the entity should sufficiently exceed the affinity of the attachment molecule/peptide for other molecules that may be present in a solution (such as a biological sample) to which the attachment molecule/entity complex is exposed to minimize displacement of the entity. This can be accomplished by screening the attachment molecules for non-specific binding to non-entities in a sample. For example if it is a blood sample, one may screen to eliminate those attachment molecules that bind hemoglobin. Selectivity of the attachment molecule/peptide may not be critical under conditions where only a few components are present, as, for example, in a standard immunoassay. In some embodiments the selected attachment molecules may upon binding to the entity, affect the allosteric configuration or an electrostatic, electrodynamic, and/or chemical microenvironment in a way that enhances, inhibits or otherwise affects an or other property of interest.

The present invention is particularly useful for attaching antibodies or other large entities to a support. Two-dimensional arrays used in clinical diagnostics or proteomics frequently utilize antibodies as probes for protein or molecule/peptide target molecules. With the present supports and methods, antibodies bind to the support in an orientation that optimizes assay sensitivity.

As was mentioned above, all or part of the entity may be bound to the attachment molecule before, during or after binding of the attachment molecule to the support. Certain embodiments are directed to kits providing attachment molecules bound to a support for use in assaying for the presence of a particular target in a biological sample, or any other use. In one embodiment the kit includes a support to which the appropriate attachment peptide/molecule for immobilizing a known entity that binds specifically to a known target is already bound. The user may have a supply of the entity which can be added to the support at the time of use. In some embodiments attachment peptides or other attachment molecules are supplied, optionally together with buffers and/or other compositions, with the user supplying both the support and the entities to be immobilized. In another embodiment the kit includes a support to which attachment peptides/molecules and entities are already bound. In some embodiments the support with the attachment molecule or attachment molecule-entity surface is kept wet. In some cases the support/attachment molecule or attachment molecule/entity surface is dry and can either be used dry (for example to bind to targets in a gas phase), or can be hydrated to the desired level by the user.

In some embodiments the kit includes an attachment molecule/peptide-functionalized surface and a separate supply of the entity to be applied to the support by the user at the desired time of use. In another embodiment the kit includes a solution of entity bound to the attachment peptide that is ready for application to the support, and optionally includes the support. In some embodiments the support is coated with a polymer coating that further optionally includes a linker molecule bound to the polymer that facilitates binding of the attachment peptide/molecule.

Support Materials for Use in the Present Inventions

The support materials for use in the present invention can comprise a wide range of material, either biological, nonbiological, organic, inorganic, or a combination of any of these. For example, the support material may be a polymerized Langmuir Blodgett film, functionalized glass, Si, Ge, GaAs, GaP, SiO2, SiN4, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly (lactide coglycolide), polyanhydrides, poly(methyl methacrylate), poly(ethylene-co-vinyl acetate), polysiloxanes, polymeric silica, latexes, dextran polymers, epoxies, polycarbonate, or combinations thereof. Support materials can be planar crystalline support materials such as silica based support materials (e.g. glass, quartz, or the like), or crystalline support materials used in, e.g., the semiconductor and microprocessor industries, such as silicon, gallium arsenide and the like. Silica aerogels can also be used as support materials, and can be prepared by methods known in the art. Aerogel support materials may be used as free standing substrates or as a surface coating for another support material.

The support material can take any form or shape and typically is a plate, slide, bead, pellet, disk, particle, strand, precipitate, membrane, optionally porous gel, sheets, tube, sphere, container, capillary, pad, slice, film, chip, multiwell plate or dish, optical fiber, etc. Although typically the support material takes an inanimate form, for some attachment peptide applications such as flow cytometry or in situ hybridization, it can be any form that is rigid or semi-rigid. The support material may contain raised or depressed regions on which a capture probe is located. The surface of the support material can be etched using well known techniques to provide for desired surface features, for example trenches, v-grooves, mesa structures, or the like.

Surfaces on the support material can be composed of the same material as the interior part of the support or can be made from a different material, and can be coupled to the interior support material by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed support materials. In one embodiment, the surface is optically transparent and can have surface Si—OH functionalities, such as those found on silica surfaces.

Glass or plastic microscope slides have commonly been used as solid matrix supports for microarray analysis. Opaque matrix-coating materials used to produce microarrays include nylon, PVDF (polyvinylidene fluoride) and nitrocellulose. Nitrocellulose, a traditional polymer substrate in use for more than 50 years, can be used for microarray attachment applications. (E.g., Tonkinson and Stillman, Frontiers in Bioscience 7:c1-12, 2002.) Opaque nitrocellulose has been extensively used to immobilize proteins and nucleic acids for biomolecular analysis. Nitrocellulose immobilizes molecules of interest in near quantitative fashion and allows for short and long term storage. Nitrocellulose also allows for solution phase target species to efficiently bind to immobilized entities.

In some embodiments the support may be of any suitable composition to which the attachment molecule may be applied. It may be pretreated or functionalized prior to application of the attachment/molecule peptide to facilitate binding of the attachment molecules, or for any other desired purpose, such as fostering conditions favorable for the activity or any other desired property of the entity or avoiding undesired interactions with other entities. Many such surface treatments and/or functionalizations are known in the art and selection of a suitable treatment and/or functionalization will depend upon the identity and characteristics of the attachment molecule/peptide and entity and upon the attendant conditions and desired activity.

Labels

In some embodiments labels can be used to detect binding of the entity to the attachment peptide in the screening method, and for detecting binding of a target to the entity. In various embodiments of the invention, labeled targets and entities may be prepared by any methods known in the art. In certain embodiments, a label moiety is incorporated into a target or entity (e.g., peptide, protein, and oligonucleotide) during synthesis. In other embodiments, labels are attached by covalent, noncovalent, ionic, van der Waals, hydrogen bonding or other forces. Methods for attaching fluorescent or other labels to targets or entities are known in the art and any such known method may be used. In particular embodiments, a target analyte molecule is biotinylated and may bind to an avidin or streptavidin-conjugated fluorophore. Fluorophores and conjugated fluorophores may be obtained from commercial sources, such as Molecular Probes, Inc. (Eugene, Oreg.).

Labels of use in the present invention include any composition detectable by electrical, optical, spectrophotometric, photochemical, biochemical, immunochemical, or chemical techniques. Labels may include, but are not limited to, conducting, luminescent, fluorescent, chemiluminescent, bioluminescent and phosphorescent labels, chromogens, enzymes or support materials. Fluorescent molecules suitable for use as labels include, but are not limited to, dansyl chloride, rhodamineisothiocyanate, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5,6-FAM, fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red. A variety of other known fluorescent or luminescent labels may be utilized. (See, e.g., U.S. Pat. No. 5,800,992; U.S. Pat. No. 6,319,668.).

Detection/Evaluation of Activity and/or Property

An activity or property of an entity or target may be detected and/or evaluated by any method operable to provide a measurement or estimate reasonably related to the activity or property. In some embodiments where an activity or property sought to be detected or evaluated is the ability of an entity to bind a target, detection or evaluation may include detecting, and optionally quantifying, a label associated with the target at or in proximity to a locus occupied by the entity. In some embodiments where it is desired to detect or evaluate the ability of an attachment molecule to immobilize an entity, detection or evaluation includes detecting, and optionally quantifying, a label associated with the entity, at or in proximity to a locus occupied by the attachment molecule. In some embodiments detection or evaluation of the presence of a target bound to an entity includes detecting, and optionally quantifying, the binding of target present in solution phase to an entity immobilized on a surface using techniques such as surface plasmon resonance or Corning Epic technology. In some embodiments where an activity or property sought to be detected or evaluated is the enzymatic activity of an enzyme, detection or evaluation may include detecting, and optionally quantifying, the production of product or the depletion of substrate, directly or via a suitable reporter system. In some embodiments where an activity or property sought to be detected or evaluated is the tendency of an entity to react with a target, detection or evaluation may include detecting, and optionally quantifying, the production of a reaction product or the depletion of a reactant, directly or via a suitable reporter system. In some embodiments the activity or property sought to be detected or evaluated is a cell state or process where entity or target that is a cell, virus, organelle, or other biological entity or target. In some embodiments the activity or property is a physical property of an entity.

Bioactive Agents

Bioactive agents that are potential entities and targets encompass numerous chemical classes, though typically they are organic molecules, preferably small organic compounds having a molecular weight of more than 100 and less than about 2,500 daltons. Bioactive agents include functional groups necessary for structural interaction with proteins, particularly hydrogen bonding, and typically include at least an amine, carbonyl, hydroxyl or carboxyl group, preferably at least two of the functional chemical groups. The bioactive agents often include cyclical carbon or heterocyclic structures and/or aromatic or polyaromatic structures substituted with one or more of the above functional groups. Bioactive agents are also found among biomolecules including peptides, saccharides, fatty acids, steroids, purines, pyrimidines, derivatives, structural analogs or combinations thereof. Particularly preferred are peptides.

Bioactive agents are obtained from a wide variety of sources including libraries of synthetic or natural compounds. For example, numerous means are available for random and directed synthesis of a wide variety or organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In other embodiments, the bioactive agent is a naturally occurring protein or fragment or variant of a naturally occurring protein. Thus, for example, cellular extracts containing proteins, or random or directed digests of proteinaceous cellular extracts, may be used. In this way libraries of prokaryotic and eukaryotic proteins may be made for screening against one of the various proteins. Libraries of bacterial, fungal, viral, and mammalian proteins including human proteins can be used.

In one embodiment, the library is fully randomized, with no sequence preferences or constants at any position. In one embodiment, the library is biased. That is, some positions within the sequence are either held constant, or are selected from a limited number of possibilities. For example, in one embodiment the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines. As described above generally for proteins, nucleic acid bioactive agents may be naturally occurring nucleic acids, random nucleic acids, or "biased" random nucleic acids. For example, digests of prokaryotic or eukaryotic genomes may be used as is outlined above for proteins.

In a preferred embodiment, the bioactive agents are obtained from combinatorial chemical libraries, a wide variety of which are available in the literature. These include a collection of diverse chemical compounds generated in a defined or random manner, generally by chemical synthesis. Millions of chemical compounds can be synthesized through combinatorial mixing.

The determination of the binding of a target bioactive agent to an entities may be done in a number of ways. In some embodiments, the bioactive agent is labeled, and binding determined directly. For example, this may be done by attaching all or a portion of an entity to a solid support using the described attachment molecules, adding a labeled bioactive agent (for example a bioactive agent having a fluorescent label), washing off excess reagent, and determining whether the label is present on the solid support. Various blocking and washing steps may be utilized as is known in the art.

The bioactive agent may be directly or indirectly labeled with a label that provides a detectable signal, e.g. a radioisotope (such as $H^3$, $C^{14}$, $P^{32}$, $P^{33}$, $S^{35}$, or $I^{125}$), a fluorescent or chemiluminescent compound (such as fluorescein isothiocyanate, rhodamine, or luciferin), an enzyme (such as alkaline phosphatase, beta-galactosidase or horseradish peroxidase), antibodies, particles such as magnetic particles, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures. The label can directly or indirectly provide a detectable signal. In some embodiments, only one of the components is labeled. Alternatively, more than one component may be labeled with different labels.

EXAMPLES

Example 1

Selecting Attachment Peptides for Carbonic Anhydrase that Preserve the Ability to Bind Dansylamide The following series of experiments demonstrates the selection of attachment peptides capable of immobilizing an entity on a support in an orientation that leaves the active site of the entity open and that does not interfere with the activity of interest. The entity was carbonic anhydrase, and the activity being measured was the ability of a known carbonic anhydrase inhibitor, dansylamide, to bind carbonic anhydrase.

Candidate peptides were identified by comparing the results of two peptide microarray experiments. Each experiment was performed using identical robotically spotted peptide microarrays, each exposing approximately 6,000 distinct peptides, with each spot on the microarray comprising a single peptide sequence. The peptides were each 20 residues in length, synthesized according to sequences determined by a pseudorandom computational process in which each of the 20 naturally occurring amino acids except cysteine had an equal probability of being represented at each position except the last three C-terminal positions, which were glycine-serine-cysteine for all peptides tested. The array surface was coated with poly-lysine, and the peptide probes were bound to the poly-lysine at the C-terminal cysteine via a maleimide linker (SMCC).

In the first experiment, fluorescently labeled carbonic anhydrase was applied to the microarray, together with *E. coli* lysate labeled with a second fluorophore distinguishable from that used to label the carbonic anhydrase. Peptides to which the carbonic anhydrase bound were identified by observing the fluorescence signal of the carbonic anhydrase in comparison to that of the *E. coli* lysate competitor. In the second experiment, labeled carbonic anhydrase that had been pre-incubated with dansylamide was applied to the microarray, again with *E. coli* lysate, and peptides to which the carbonic anhydrase-dansylamide complex bound were identified. The first experiment identified peptides preferentially binding carbonic anhydrase, but these could potentially include peptides that may have bound in an orientation that would prevent the dansylamide inhibitor from binding to the carbonic anhydrase. The second experiment identified peptides binding the carbonic anhydrase in an orientation that is not prevented by the presence of the dansylamide inhibitor. However, the peptides identified in the second experiment could also include peptides binding in a manner requiring the presence of the dansylamide (such as those binding entirely or partially to the dansylamide rather than the carbonic anhydrase). 13 peptides were selected, based on the results of the two experiments that bound both the carbonic anhydrase alone (experiment 1) and the carbonic anhydrase-dansylamide complex (experiment 2). These peptides are listed in FIG. 6A, and were selected as candidates likely to bind carbonic anhydrase in an orientation that would not interfere with the active site.

Figure 6A:
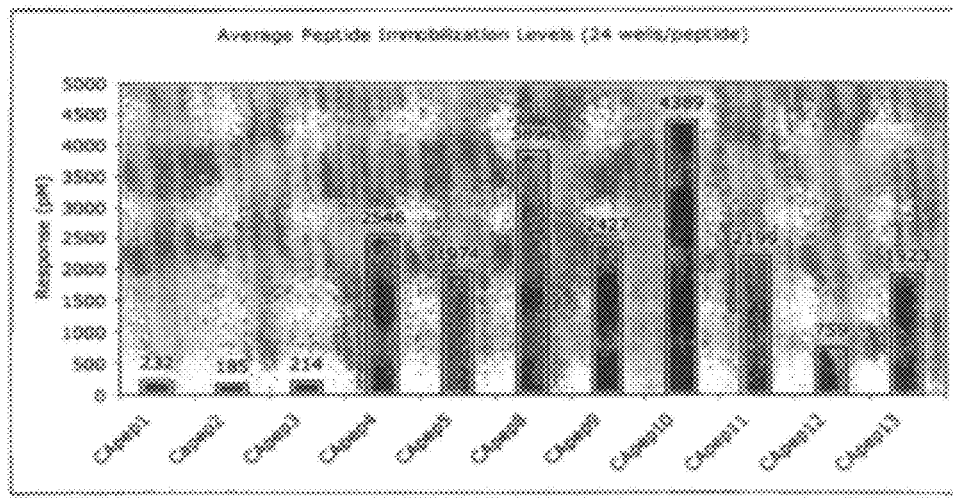
FIG. 6(a) shows the wavelength shift in picometers observed in an Epic experiment for each of 11 attachment peptides.
Figure 6B:
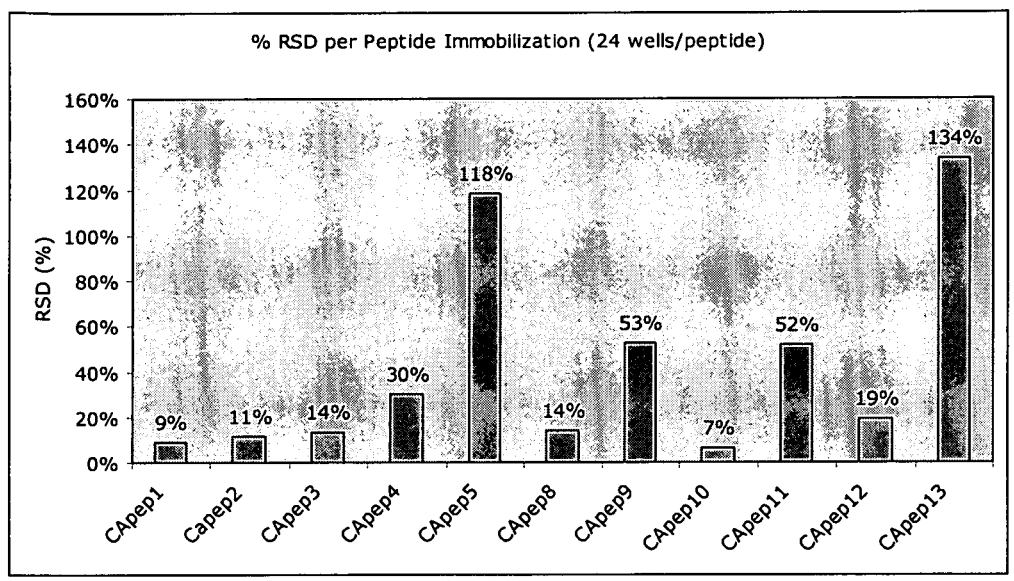
FIG. 6(b) shows the standard deviation among 24 replicates.
Figure 6C:
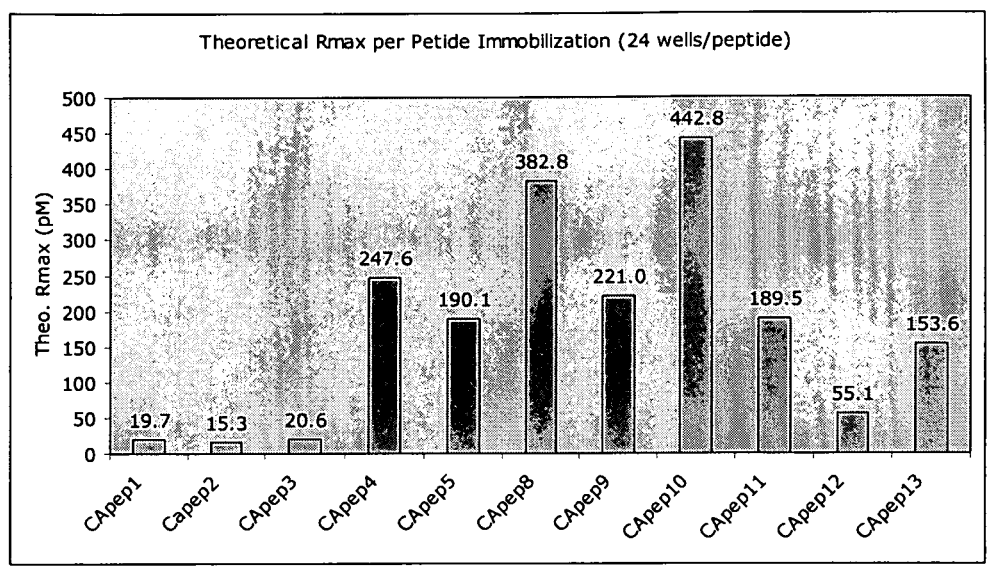

The selected candidate peptides were applied to the wells of a Corning Epic System 384-well microplate by linking the C-terminal cysteines of the peptides to surface amines of the Epic microplate wells via the maleimide and amine moieties, respectively, of a BMPH linker (Pierce). The immobilization of the peptides to the Epic microplate wells without carbonic anhydrase was first evaluated to identify any peptides binding poorly to the well surface, and to provide a basis for computing the maximum wavelength shift theoretically obtainable with optimal binding of the carbonic anhydrase to the peptides at a concentration sufficient to saturate. FIG. 6(a) shows the wavelength shift in pm observed in an Epic experiment for each of 11 peptides (two of the original 13 having been eliminated due to problems relating to their synthesis and/or attachment). FIG. 6(b) shows the standard deviation among 24 replicates. Peptides CA1, CA2, CA3, and CA12 showed a relatively low wavelength shift, indicating that there was a low mass present on the surface, therefore these peptides were rejected as attachment peptides for carbonic anhydrase. This could reflect inadequate binding to the surface due to poor solubility of the poorly binding peptides. For peptides CA5 and CA13 the standard deviation of the wavelength shift among replicates was sufficiently high to indicate poor reproducibility.

Carbonic anhydrase was applied in Epic microplate wells in which the selected peptides had been pre-applied to the well surface, in groups of four replicate wells and in carbonic anhydrase concentrations ranging from 31 nM to 1 µM. Observed wavelength shifts after 30 minute incubation of the indicated concentrations of carbonic anhydrase with peptides CA4, CA8, CA9, CA10, CA11, and CA12 are shown in FIG.

Figure 7B:
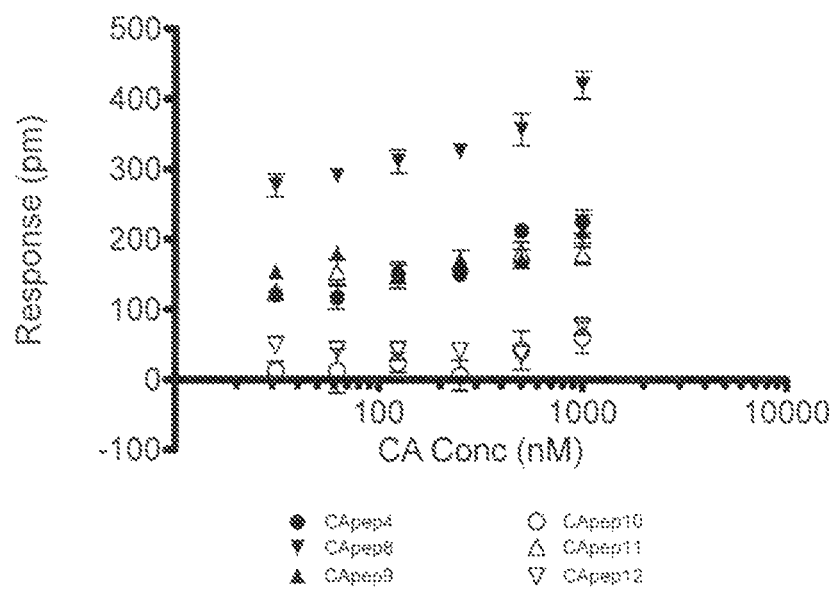
FIG. 7 Observed wavelength shifts after a 30 minute incubation of the indicated concentrations of carbonic anhydrase with attachment peptides CA4, CA8, CA9, CA10, CA11, and CA12 are shown in FIG. 7(a) (absolute wavelength shift, pm; 7(b) shows wavelength shifts after 180 minute incubation.
Figure 7C:
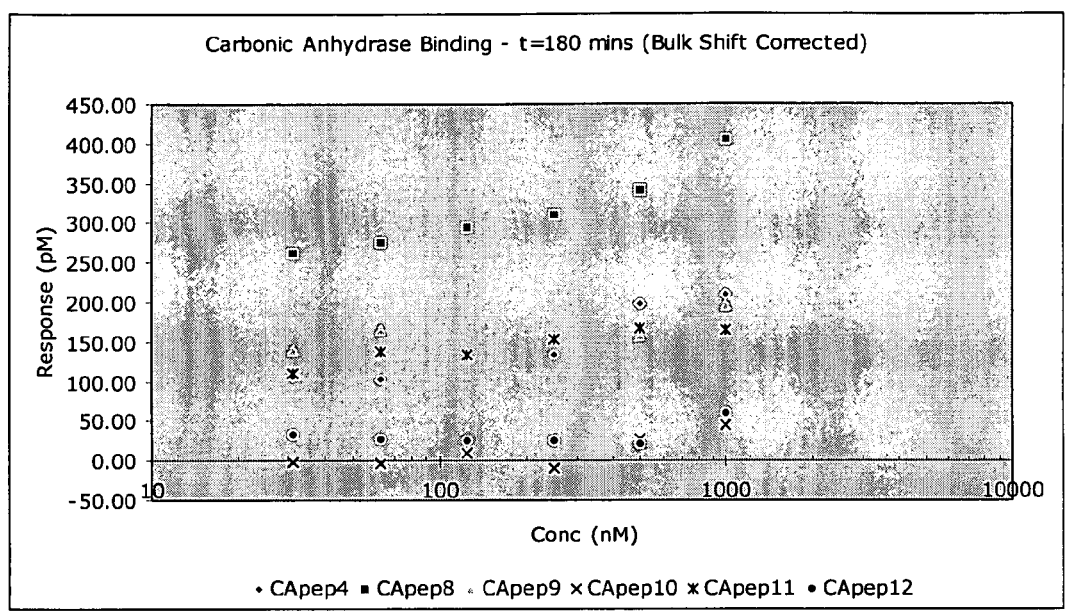
Figure 7D:
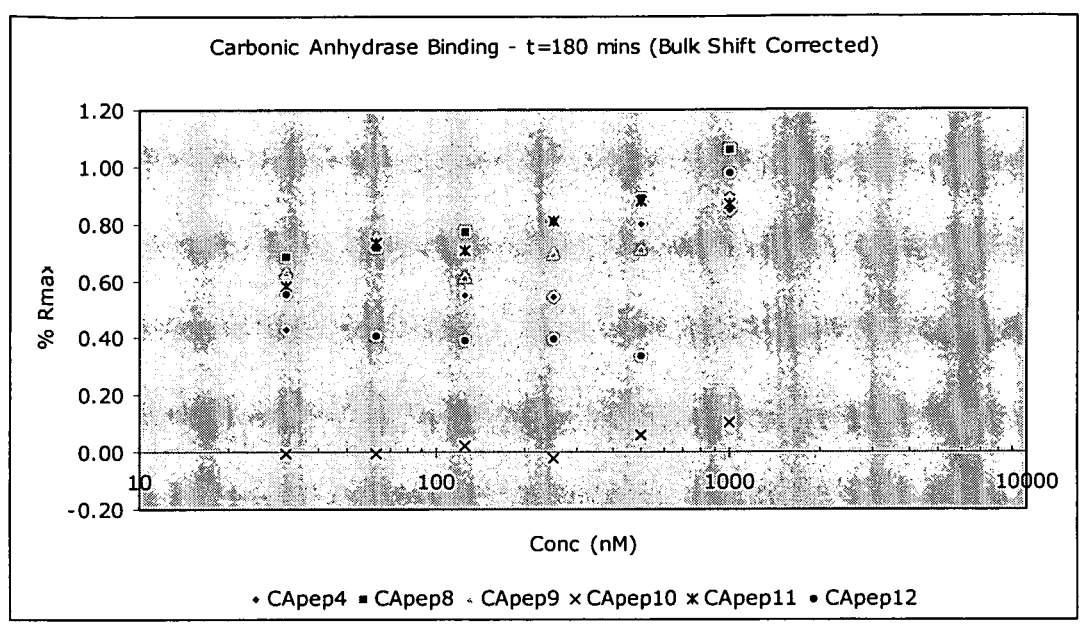

7(a). Wavelength shifts after 180 minute incubation are shown in FIG. 7(b). Binding of carbonic anhydrase at 1 μM to peptides CA4, CA8, CA9, CA11, and CA12 produced wavelength shifts which persisted even after 180 minutes incubation, demonstrating that, after linkage of the peptides to the Epic well surface in typical assay conditions, these peptides were able to immobilize the carbonic anhydrase and the immobilization was stable over a period of three hours.

Figure 8:
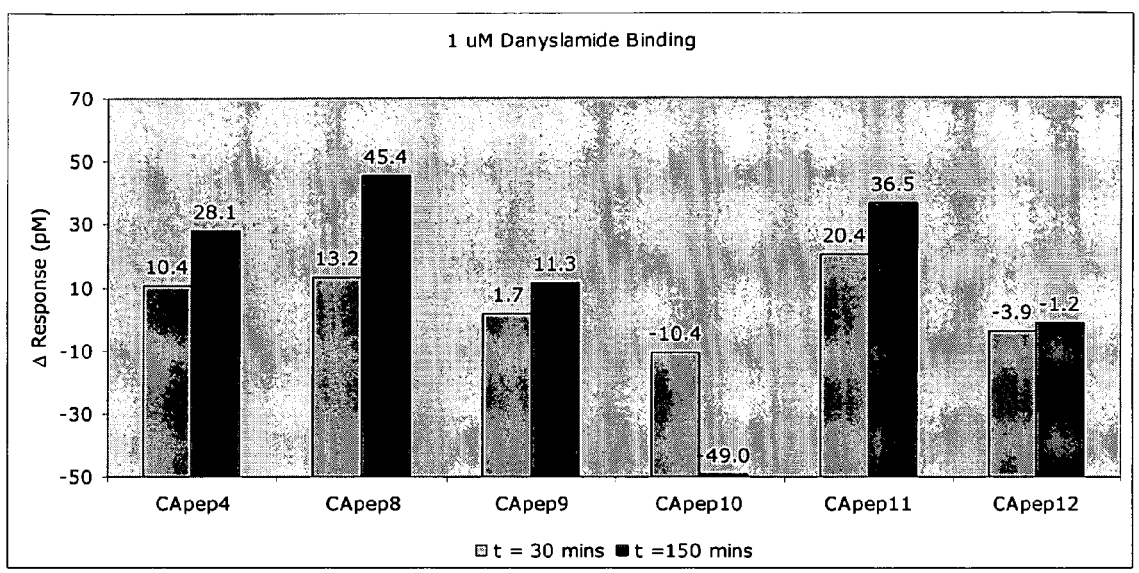
FIG. 8 shows the additional wavelength shift upon application of the dansylamide after 30 minutes and 150 minutes, respectively.

Dansylamide, a known inhibitor of carbonic anhydrase, was applied to a range of concentrations (31 nM to 1 μM) of carbonic anhydrase immobilized in Epic wells by peptides CA4, CA8, CA9, CA10, CA11, and CA12. FIG. 8 shows the additional wavelength shift upon application of the dansylamide after 30 minutes and 150 minutes, respectively. Wavelength shifts on the order of approximately 10 to 20 pm were observed upon application of the dansylamide to carbonic anhydrase immobilized at 1 μM concentration on peptides CA4, CA8, and CA11, confirming that the carbonic anhydrase was immobilized in an orientation that preserved the availability of the binding site (active site) and ability of the enzyme to consistently bind the inhibitor dansylamide, and confirming that the attachment peptides were able to immobilize carbonic anhydrase in the wells of an Epic plate in a manner such that binding of dansylamide to the carbonic anhydrase was readily detectable by the Epic technology.

Figure 9:
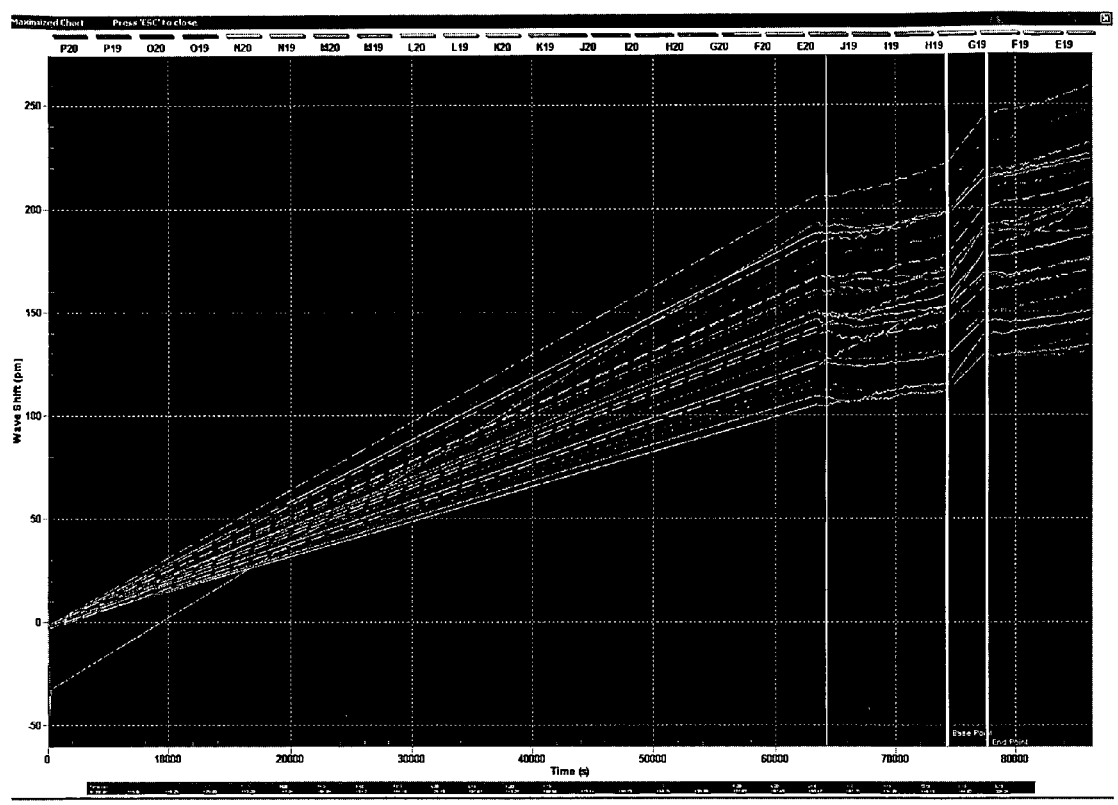
FIG. 9 shows the time course of the wavelength shift for each of four replicates at each of the six carbonic anhydrase concentrations, for peptide CA11, upon application of carbonic anhydrase (at time 64000 sec), then 1 μM dansylamide (at time 74000 sec). For nearly all replicates, a shift on the order of 20 pm was observed upon application of the dansylamide.

FIG. 9 shows the time course of the wavelength shift for each of four replicates at each of the six carbonic anhydrase concentrations, for peptide CA11, upon application of carbonic anhydrase (at time 64000 sec), then 1 μM dansylamide (at time 74000 sec). For nearly all replicates, a shift on the order of 20 pm was observed upon application of the dansylamide.

Example 2

Attachment peptides capable of immobilizing beta-galactosidase in a manner enhancing or inhibiting the enzyme's activity were selected by directly observing the activity of enzyme immobilized to spots of a peptide microarray. The experiment was performed using a robotically spotted peptide microarray exposing approximately 7,000 distinct peptides, with each spot on the microarray comprising a single peptide sequence, and each peptide present in three replicate spots. The peptides were each 20 residues in length, synthesized according to sequences determined by a pseudorandom computational process in which each of the 20 naturally occurring amino acids except cysteine had an equal probability of being represented at each position except the last three C-terminal positions, which were glycine-serine-cysteine for all peptides. The array surface was coated with poly-lysine, and the attachment peptides were bound to the poly-lysine at the C-terminal cysteine via a maleimide linker (SMCC).

The array was blocked against non-specific binding (to prevent or reduce binding of enzyme and/or label to array loci that do not have specific affinity for the enzyme) by applying 350 μL blocking buffer (5 mL of 30% BSA, 6.9 μL mercaptohexanol, 25 μL Tween20, in 1×PBS to 50 ml) and incubating for one hour in a humidity chamber. (Other means of blocking non-specific binding are known in the art and any operable method may be used.) The array was then washed once with TBST and twice with water, and dried by centrifugation. 330 μL 10 nM Alexa647-labeled beta-galactosidase in 3% BSA, 0.05% Tween20, and 1×PBS was applied to the array. The array with the enzyme was then sealed using an AbGene gene frame and slide cover, and incubated for one hour in a humidity chamber in the dark. After one hour the slide cover was removed and the array washed three times with 1×TBST (pH 7.6), 5 minutes each wash. This was followed by three washes with 1 mM potassium phosphate buffer (pH 7.6), 5 minutes each wash. The array was then read using a standard array reader (PerkinElmer).

Figure 11:
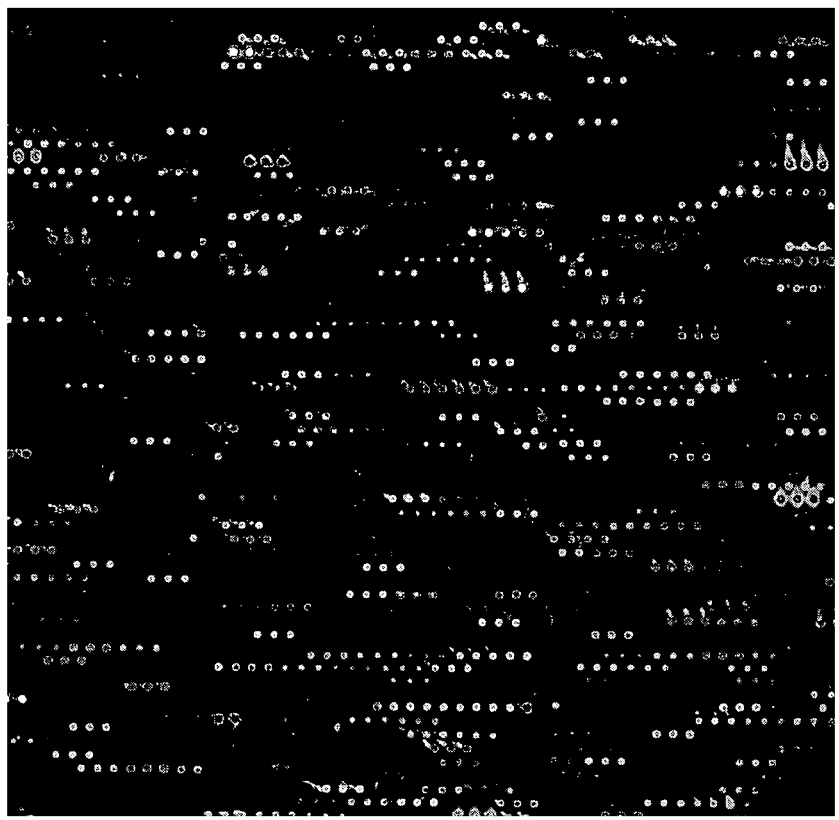
FIG. 11 shows a false color representation of measured Alexa647 intensities for a representative region of the array surface (colors ranging from white through red, yellow, blue, and black, with white corresponding to the highest intensities and black to the lowest). The reading showed that the labeled beta-galactosidase bound to attachment peptides located at a number of discrete spots of the array.

FIG. 11 shows a false color representation of measured Alexa647 intensities for a representative region of the array surface (colors ranging from white through red, yellow, blue, and black, with white corresponding to the highest intensities and black to the lowest). The reading showed that the labeled beta-galactosidase bound to attachment peptides located at a number of discrete spots of the array. Recall that each attachment peptide was represented three times on the array at different spots.

Figure 10:
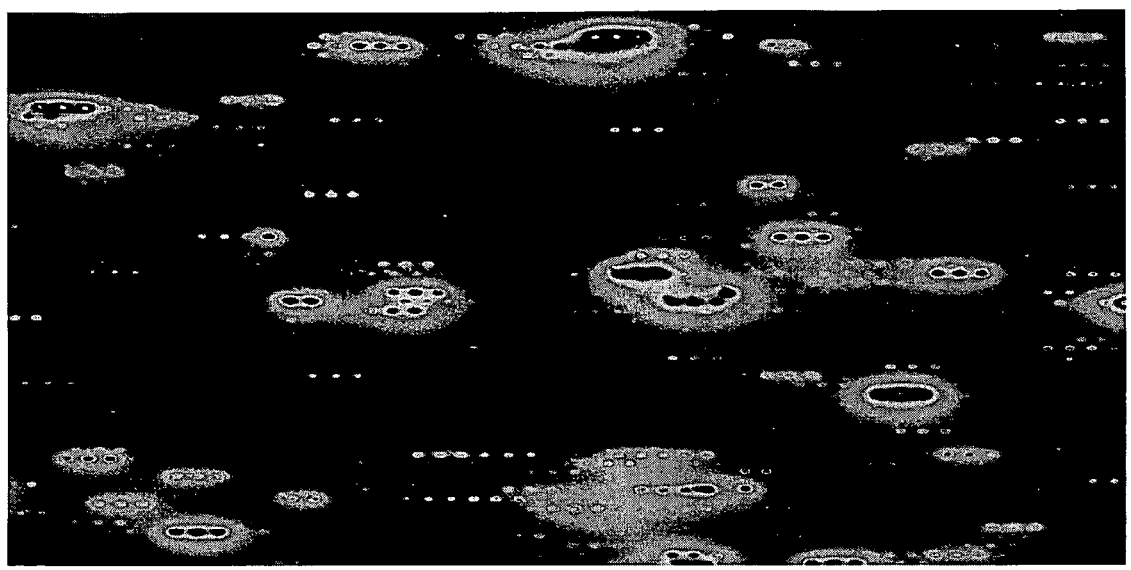
FIG. 10 shows a false color representation of measured 520 nm intensities for the same region of the array surface as shown in FIG. 11. High 520 nm fluorescence intensity levels were measured for several replicate groups of array loci, indicating a relatively high level of beta-galactosidase activity at those loci.

The same array was then coated with a thin (approximately 40-50 μm) layer of a polyvinyl alcohol (PVA) polymer hydrogel impregnated with fluorescein di-galactoside substrate (FDG). The hydrogel inhibits and/or slows diffusion of the substrate, facilitating localization and detection of the substrate's reaction with the enzyme. To produce the PVA layer, 5% (mass) PVA viscous solution in 10 mM potassium phosphate and 100 μM $MgCl_2$ buffer (pH 7.6), into which was diluted 1 μM FDG, was applied to the array by spin-coating, after which the array was placed in a humidity chamber for 15 minutes in the dark. After the incubation the array was dried under vacuum for 30 seconds. The array was again scanned for intensity of the 520 nm fluorescence that is characteristic of FDG upon hydrolysis by beta-galactosidase under 488 nm excitation. FIG. 10 shows a false color representation of measured 520 nm intensities for the same region of the array surface as shown in FIG. 11. High 520 nm fluorescence intensity levels were measured for several replicate groups of array loci, indicating a relatively high level of beta-galactosidase activity at those loci.

Figure 12:
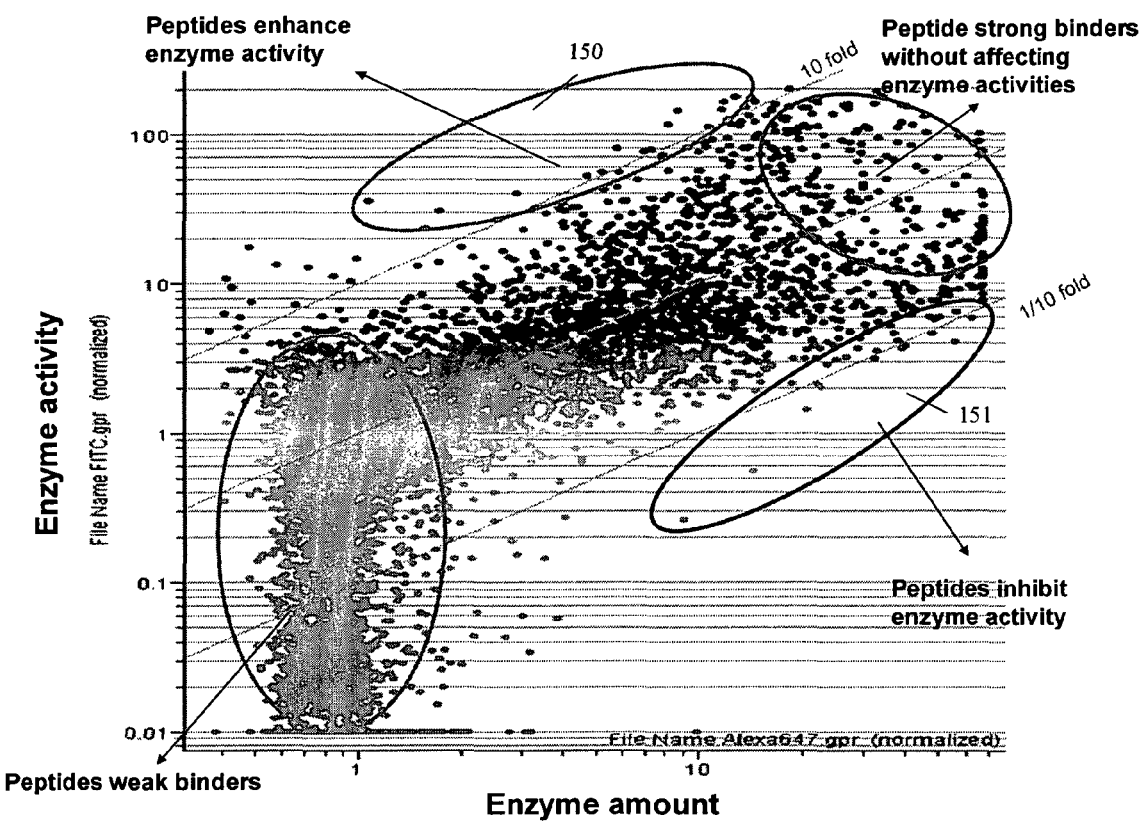
FIG. 12 shows, that the relative substrate (FDG)-hydrolyzing activity of beta-galactosidase immobilized on a microarray having a surface of attachment peptides (vertical axis) varies over a considerable range, depending upon the specific attachment peptide to which the beta-galactosidase is bound and immobilized.

The 520 nm intensities (normalized to median intensity for all loci) following incubation of FDG impregnated hydrogel were compared to the Alexa647 intensities (again normalized to median intensity for all loci) observed following the incubation of beta-galactosidase on the array prior to application of the substrate FDG/hydrogel. As FIG. 12 shows, the relative FDG-hydrolyzing activity of beta-galactosidase immobilized on array peptides (vertical axis) varies over a considerable range, depending upon the specific attachment peptide to which the beta-galactosidase is bound and immobilized. Certain peptides produced a relative increase in beta-galactosidase activity and others produced a relative decrease, after taking into account the relative levels (horizontal axis) at which various peptides bound beta-galactosidase in the absence of substrate.

Figure 13:
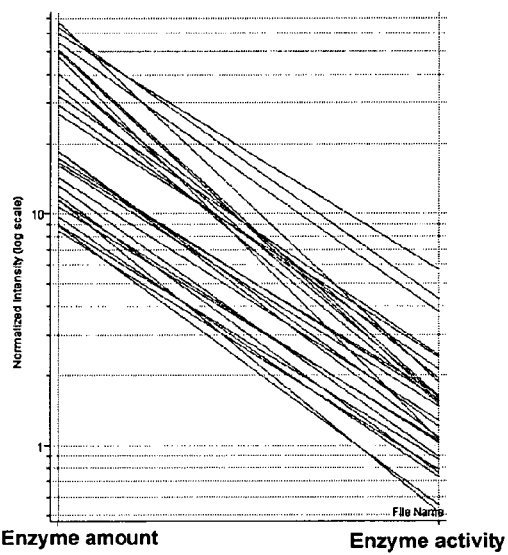
FIG. 13(a) shows the median-normalized intensity values reflecting the amount of enzyme present at different array loci and the enzyme activity for attachment peptides showing a relatively low activity even where enzyme is present at relatively high amount. This indicates that the effect of substrate immobilization by these peptides is a relative increase in activity of the enzyme entity.
FIG. 13(b) shows median-normalized intensity values reflecting amount of enzyme present on different array loci and enzyme activity for attachment peptides showing relatively high activity even where enzyme is present at relatively low amount, indicating that the effect of immobilization by these peptides is a relative decrease in activity.
Figure 13:
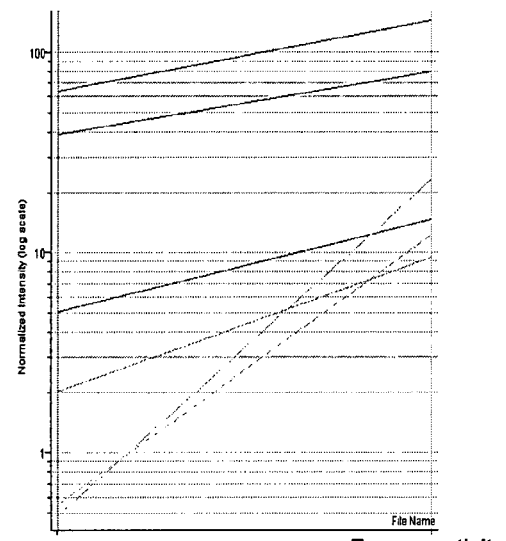

Immobilization of beta-galactosidase on certain peptides (150) resulted in relatively high 520 nm intensity even though relatively less beta-galactosidase was present at the corresponding loci (as confirmed by the relatively low Alexa647 intensity at those loci). Immobilization of beta-galactosidase on other attachment peptides (151) resulted in relatively low 520 nm intensity even though a relatively high quantity of beta-galactosidase was present (as confirmed by the relatively high Alexa647 intensity at those loci). FIG. 13 shows median-normalized intensity values reflecting the amount of enzyme present on different array loci and the corresponding enzyme activity at each locus. FIG. 13a shows attachment peptides where enzyme is present in relatively high amounts, but relatively low activity is detected. This indicates that the effect of substrate immobilization by these peptides orients the enzyme in a way that decreases its ability to hydrolyze its substrate. FIG. 13(b) shows median-normalized intensity values reflecting the amount of enzyme present on different array loci showing relatively high enzyme activity even where the enzyme is present at in relatively low amounts, indicating that the effect of immobilization by these peptides is a relative increase in activity. Thus if the goal is to reduce or minimize enzyme activity the peptides in 13(*a*) should be selected, and if the goal is to optimize enzyme activity, then the peptides of 13(*b*) should be selected.

Figure 14:
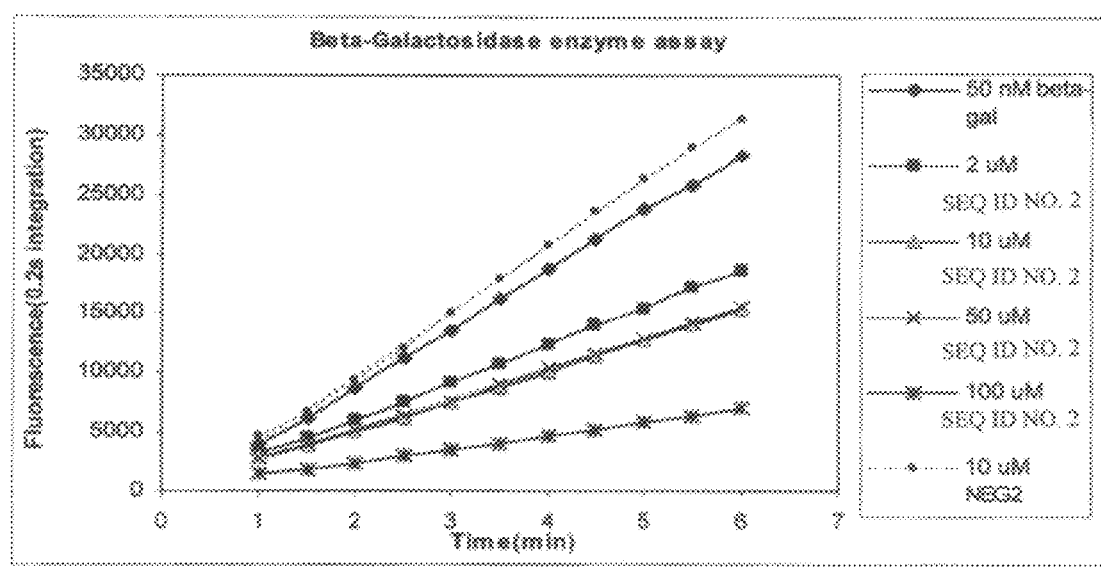
FIG. 14 shows the enzyme activity of the entity beta-galactosidase when bound to the selected peptide having the sequence FRNFPVPVIFRYLNPWPGSC (SEQ ID NO. 2) in solution phase. The enzyme was preincubated with varying concentrations of the peptide for 0.5 hour before adding the substrate FDG. 520 nm fluorescence was measured upon 488 nm excitation at a series of time points.

The enzyme activity of the entity beta-galactosidase when bound to the selected peptide having the sequence FRNF-PVPVIFRYLNPWPGSC (SEQ ID NO. 2), was evaluated in solution phase by preincubating varying concentrations of the peptide with beta-galactosidase for 0.5 hour, then adding substrate FDG in solution and measuring 520 nm fluorescence upon 488 nm excitation at a series of time points. FIG. 14 compares the increase in fluorescence intensity over time upon adding 5 µM FDG to 50 nM beta-galactosidase in buffer (10 mM potassium phosphate and 100 µM MgCl$_2$, pH 7.6) preincubated with 2 µM 160, 10 µM 161, 50 µM 162, and 100 µM 163 of the selected peptide, to fluorescence intensity upon adding 5 µM FDG to beta-galactosidase (in buffer) alone (164) and with beta-galactosidase preincubated with a comparison attachment peptide (165) (sequence ESVPTDLPM-DTMEGKNWGSC (SEQ ID NO. 14) in buffer). The measured 520 nm fluorescence intensity, which indicates the amount of enzyme activity of the entity when bound to the selected peptide, at all concentrations was significantly lower than that for beta-galactosidase alone, indicating that the selected peptide inhibited the activity of beta-galactosidase in solution phase. The 520 nm intensities measured for beta-galactosidase preincubated with the comparison peptide were slightly higher than for beta-galactosidase alone, indicating that the comparison peptide slightly enhanced the activity of beta-galactosidase in solution phase.

Applicant herein expressly incorporates by reference all of the following materials identified in each numbered paragraph below. The incorporated materials are not necessarily "prior art" but are provided as non essential support for the inventions.

1. U.S. Pat. No. 4,888,285 to Nishimura (1989).
2. U.S. Pat. No. 5,252,719 to Takeda (1993).
3. U.S. Pat. No. 5,766,908 to Klein (1998).
4. U.S. Pat. No. 6,773,928 to Yin (2004).
5. U.S. Pat. No. 7,078,192 to Linder (2006).
6. U.S. Pat. No. 7,105,488 to Tarasova (2006).
7. U.S. Patent Publication Number 2003175918 Basheer (2003).
8. U.S. Patent Publication Number 2004014242 Iwakura (2004).
9. U.S. Patent Publication Number 2006003381 Gilmore (2006).
10. PCT Publication Number WO1992008788 Sliger (1992).
11. PCT Publication Number WO1995009058 Vakula (1995).
12. PCT Publication Number WO2000061789 Bachovchin (2000).
13. PCT Publication Number WO2004090154 Campbell (2004).
14. Corning® Epic™ System—Development of a Label-Free High Throughput Screening (HTS) System for Biochemical and Cell-Based Drug Discovery, Publication Number CLS-AN-070, Corning Incorporated, Corning N.Y., (2005).
15. Benoiton N L, Chemistry of Peptide Synthesis, CRC Press, Boca Raton Fla. (2005).
16. Jones J, Amino Acid and Peptide Synthesis (Oxford Chemistry Primers 7), Oxford UK (2002).
17. Jung G, Combinatorial Peptide and Non-Peptide Libraries, Verlag Chemie, Weinheim Germany (1996).
18. Cabilly S, Combinatorial Peptide Library Protocols (Methods in Molecular Biology) Humana Press, Totowa N.J. (1998).
19. Müller U R and Nicolau D V, Microarray Technology and its Applications (Biological and Medical Physics, Biomedical Engineering), Springer (2004).
20. Predki P F, Functional Protein Microarrays in Drug Discovery, CRC Press, Boca Raton Fla. (2007).
21. De Vos et al, Chiral Catalyst Immobilization and Recycling, Wiley-VCH, Weinheim Germany (2000).
22. Panicker R, et al, Recent Advances in Peptide-Based Microarray Technologies, Combinatorial Chemistry & High Throughput Screening, 7 547-556 (2004).
23. Sun H et al, Recent developments in microarray-based enzyme assays: from functional annotation to substrate/inhibitor fingerprinting, Anal Bioanal Chem 386 416-426 (2006).
24. Bickerstaff G F Ed. Immobilization of Enzymes and Cells, Humana Press, Totowa N.J. (1997).
25. Guibault G G and Mascini M, Uses of Immobilized Biological Compounds, Kluwer Academic Publishers, Dordrecht, The Netherlands (1993).
26. Fodor S P A et al, Light-directed, spatially addressable parallel chemical synthesis, Science 251 767-773 (1991).
27. Schena M et al, Quantitative Monitoring of Gene Expression Patterns with a Complementary DNA Microarray, Science 270 467-470 (1995).
28. MacBeath G et al, Printing Small Molecules as Microarrays and Detection Protein-Ligand Interactions en Masse, J Am Chem Soc 121 7967-7968 (1999).
29. MacBeath G and Schreiber S L, Printing proteins as microarrays for high-throughput function determination, Science 289 1760-1763 (2000).
30. Chen G Y J et al, Array-based technologies and their applications in proteomics, Curr Top Med Chem 3 705-724 (2003).
31. Chattopadhaya S and Yao S Q, Enzyme assays on chips, In: Enzyme assays: high-throughput screening, Genetic Selection and fingerprinting, Reymond J L ed. Wiley (2006).
32. Panicker R C et al, Advanced analytical tools in proteomics, Anal Chim Acta 556 69-79 (2006).
33. Uttamchandani M et al, Protein and small molecule microarrays: powerful tools for high-throughput proteomics, Mol Bio Syst 2 58-68 (2006).
34. Joos T O et al, A microarray enzyme-linked immunosorbent assay for autoimmune diagnostics, Electrophoresis 21 2641-2650 (2000).
35. Ge H, UPA, a universal protein array system for quantitative detection of protein-protein, protein-DNA, protein-RNA and protein ligand interactions, Nucleic Acids Res 28 e3 (2000).
36. Vijayendran R A and Leckband D E A quantitative assessment of heterogeneity for surface-immobilized proteins, Anal Chem 73 471-480 (2001).
37. Lesaicherre M L et al, Intein-mediated biotinylation of proteins and its application in a protein microarray, J Am Chem Soc 124 8768-8769 (2002).
38. Lue R Y P et al, Versatile protein biotinylation strategies for potential high-throughput proteomics, J Am Chem Soc 126 1055-1062 (2004).
39. Hodneland C D et al, Selective immobilization of proteins to self-assembled monolayers presenting active site-directed capture ligands, PNAS USA 99 5048-5052 (2002).
40. Kindermann M et al, Covalent and selective immobilization of fusion proteins, J Am Chem Soc 125 7810-7811 (2003).

41. Yin J et al, Labeling proteins with small molecules by site-specific posttranslational modification, J Am Chem Soc 126 7754-7755 (2004).
42. Tan L P et al, Expanding the scope of site-specific protein biotinylation strategies using small molecules, Bioorg Med Chem Lett 14 5735-5738 (2004).
43. Girish A et al, Site-specific immobilization of proteins in a microarray using intein-mediated protein splicing, Bioorg Med Chem Lett 15 2447-2451 (2005).
44. Zhang K et al, Artificial polypeptide scaffold for protein immobilization, J Am Chem Soc 127 10136-10137 (2005).
45. Watzke et al, Angew Chem Int Ed 45 1408 (2006).
46. Kwon Y et al, Agnew Chem Intl Ed 45 1726 (2006).
47. Frank R, Spot-synthesis: an easy technique for the positionally addressable, parallel chemical synthesis on a membrane support, *Tetrahedron* 48 9217-9232 (1992).
48. Falsey J R et al, Peptide and small molecule microarray for high throughput cell adhesion and functional assays, Bioconj Chem 12 346-53 (2001).
49. Houseman B T et al, Peptide chips for the quantitative evaluation of protein kinase activity, Nat Biotechnol 20 270-274 (2002).
50. Houseman B T et al, Maleimide-Functionalized Self-Assembled Monolayers for the Preparation of Peptide and Carbohydrate Biochips Langmuir 19 1522-1531 (2003).
51. Lesaicherre M L et al, Developing site-specific immobilization strategies of peptides in a microarray, Bioorg Med Chem Lett 12 2079-2083 (2002).
52. Lesaicherre M L et al, Antibody-based fluorescence detection of kinase activity on a peptide array, Bioorg Med Chem Lett 12 2085-2088 (2002).
53. Uttamchandani M et al, Combinatorial peptide microarrays for the rapid determination of kinase specificity, Bioorg Med Chem Lett 13 2997-3000 (2003).
54. Sewald N, and Jakubke H-D, Peptides: Chemistry and Biology, Wiley-VCH (2002).
55. Bailey P D, An Introduction to Peptide Chemistry, Wiley; New Ed edition (1992).
56. Bodanszky M, Peptide Chemistry: A Practical Textbook, Springer-Verlag Telos; 2 Rev Sub edition (1993).
57. Benoiton N L, Chemistry of Peptide Synthesis, TF-CRC (2005).
58. Barrett G C and Elmore D T, Amino Acids and Peptides, Cambridge University Press (1998).
59. Carey F A and Sundberg R J, Advanced Organic Chemistry, Fourth Edition—Part B: Reaction and Synthesis, Springer; 4th ed. (2001).
60. Grant G, Synthetic Peptides: A User's Guide (Advances in Molecular Biology), Oxford University Press, USA; 2nd edition (2002).
61. Pennington M W and Dunn B M. Peptide Synthesis Protocols (Methods in Molecular Biology), Humana Press; 1st edition (1994).
62. Koch J and Mahler M, Peptide Arrays on Membrane Supports: Synthesis and Applications (Springer Lab Manuals), Springer, 1st edition (2002).
63. Abelson J N et al, Methods in Enzymology, Volume 289: Solid-Phase Peptide Synthesis (Methods in Enzymology), Academic Press; 1st edition (1997).
64. Dörwald F Z, Organic Synthesis on Solid Phase: Supports, Linkers, Reactions, Wiley-VCH; 2nd edition (2002).
65. Reimer et al, Peptide arrays: from macro to micro, Curr Opin Biotechnol 13 315-320 (2002).
66. Reineke U et al, Applications of peptide arrays prepared by the SPOT-technology, Curr Opin Biotechnol 12 59-64 (2001).
67. Pellois J P et al, Peptide synthesis based on t-Boc chemistry and solution photogenerated acids, J Comb Chem 2 355-360 (2000).
68. LeProust E et al, Digital light-directed synthesis. A microarray platform that permits rapid reaction optimization on a combinatorial basis, J Comb Chem 2 349-354 (2000).
69. Houseman B T et al, Use of a label-free method for investigating protein-peptide interactions on microarrays, Nat Biotechnol 20 270-274 (2002).
70. Wenschuh H et al, Coherent membrane supports for parallel microsynthesis and screening of bioactive peptides, Biopolymers 55 188-206 (2000).
71. Wenschuh H et al, Positionally addressable parallel synthesis on continuous membranes, In *Combinatorial Chemistry: A Practical Approach*. 95-116 Fenniri H (ed.) Oxford: Oxford University Press, (2000).
72. Reineke U et al, Antigen sequence- and library based mapping of linear and discontinuous protein-protein-interaction sites by spot synthesis, Curr Top Microbiol Immunol 243 23-36 (1999).
73. Thomas D A et al, A broad-spectrum fluorescence based peptide library for the rapid identification of protease substrates, Proteomics 6 2112-2120, (2006),
74. Ercole F et al, A combinatorial approach in designing hydrophilic surfaces for solid-phase peptide synthesis, J Appl Polym Sci 89 3371-3378 (2003).
75. Bui C T et al, Acetophenone-based linker for solid-phase peptide synthesis, J Pept Sci, 6 49-56 (2000).
76. Bui C T et al, Improving the performance of an acid-labile 4-hydroxymethylphenoxyacetic acid (HMP) linker on resin and SynPhase grafted solid-supports, J Pept Sci 6 534-538, (2000).
77. Fernandez-Escamilla et al, Related Prediction of sequence-dependent and mutational effects on the aggregation of peptides and proteins, Nat Biotechnol 22 1302-1306 (2004).
78. Beyer M et al, A novel glass slide-based peptide array support with high functionality resisting non-specific protein adsorption, Biomaterials, 27 3505-3514 (2006).
79. Morphy J R et al, A novel linker strategy for solid-phase synthesis, *Tetrahedron Letters* 37 3209-3212 (1996).
80. James I W, Linkers for solid phase organic synthesis, *Tetrahedron*, 55 4855-4946 (1999).
81. Eggenweiler H-M, Linkers for solid-phase synthesis of small molecules: coupling and cleavage techniques, Drug Discovery Today 3 552-560 (1998).

What is claimed is:

1. An isolated attachment peptide having the amino acid sequence FRNFPVPVIFRYLNPWPGSC (SEQ ID NO. 2).

2. An isolated attachment peptide that is a member selected from the group consisting of SEQ ID NO. 4, SEQ ID NO. 8 and SEQ ID NO. 11.

* * * * *

UNITED STATES PATENT AND TRADEMARK OFFICE
CERTIFICATE OF CORRECTION

PATENT NO.        : 8,481,679 B2                      Page 1 of 1
APPLICATION NO. : 12/677782
DATED             : July 9, 2013
INVENTOR(S)       : Johnston et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 577 days.

Signed and Sealed this
Eighth Day of September, 2015

Michelle K. Lee
*Director of the United States Patent and Trademark Office*

SEQUENCE LISTING

<160> NUMBER OF SEQ ID NOS: 14

<210> SEQ ID NO 1
<211> LENGTH: 20
<212> TYPE: PRT

```
<213> ORGANISM: Artificial Sequence
<220> FEATURE:
<223> OTHER INFORMATION: CA1 (Carbonic Anhydrase Peptide 1)

<400> SEQUENCE: 1

Phe Asn Ala Pro Ile Trp Trp Tyr Ile Tyr Pro Arg His Val Arg His
1               5                   10                  15

Ala Gly Ser Cys
            20

<210> SEQ ID NO 2
<211> LENGTH: 20
<212> TYPE: PRT
<213> ORGANISM: Artificial Sequence
<220> FEATURE:
<223> OTHER INFORMATION: CA2 (Carbonic Anhydrase Peptide 2)

<400> SEQUENCE: 2

Phe Arg Asn Phe Pro Val Pro Val Ile Phe Arg Tyr Leu Asn Pro Trp
1               5                   10                  15

Pro Gly Ser Cys
            20

<210> SEQ ID NO 3
<211> LENGTH: 20
<212> TYPE: PRT
<213> ORGANISM: Artificial Sequence
<220> FEATURE:
<223> OTHER INFORMATION: CA3 (Carbonic Anhydrase Peptide 3)

<400> SEQUENCE: 3

His Lys His Phe Phe His His Trp His Trp Phe His Lys Arg Arg Trp
1               5                   10                  15

Phe Gly Ser Cys
            20

<210> SEQ ID NO 4
<211> LENGTH: 20
<212> TYPE: PRT
<213> ORGANISM: Artificial Sequence
<220> FEATURE:
<223> OTHER INFORMATION: CA4 (Carbonic Anhydrase Peptide 4)

<400> SEQUENCE: 4

His Trp His His Arg Trp Trp His Trp Lys His Pro His Trp
1               5                   10                  15

Arg Gly Ser Cys
            20

<210> SEQ ID NO 5
<211> LENGTH: 20
<212> TYPE: PRT
<213> ORGANISM: Artificial Sequence
<220> FEATURE:
<223> OTHER INFORMATION: CA5 (Carbonic Anhydrase Peptide 5)

<400> SEQUENCE: 5

Lys Phe His His Phe Trp Lys Trp His Trp Arg Trp His His Arg Pro
1               5                   10                  15

Phe Gly Ser Cys
            20

<210> SEQ ID NO 6
<211> LENGTH: 20
<212> TYPE: PRT
```

```
<213> ORGANISM: Artificial Sequence
<220> FEATURE:
<223> OTHER INFORMATION: CA6 (Carbonic Anhydrase Peptide 6)

<400> SEQUENCE: 6

Leu Gly Arg Met Phe Ala Tyr Arg Trp Arg Leu Lys Ile Lys His Arg
1               5                   10                  15

Leu Gly Ser Cys
            20

<210> SEQ ID NO 7
<211> LENGTH: 20
<212> TYPE: PRT
<213> ORGANISM: Artificial Sequence
<220> FEATURE:
<223> OTHER INFORMATION: CA7 (Carbonic Anhydrase Peptide 7)

<400> SEQUENCE: 7

Arg His Phe Pro Trp Phe His His Phe Phe Trp His His Lys Trp Arg
1               5                   10                  15

His Gly Ser Cys
            20

<210> SEQ ID NO 8
<211> LENGTH: 20
<212> TYPE: PRT
<213> ORGANISM: Artificial Sequence
<220> FEATURE:
<223> OTHER INFORMATION: CA8 (Carbonic Anhydrase Peptide 8)

<400> SEQUENCE: 8

Arg His Trp Lys Trp His Trp Trp Arg Arg His His Pro His His Trp
1               5                   10                  15

Phe Gly Ser Cys
            20

<210> SEQ ID NO 9
<211> LENGTH: 20
<212> TYPE: PRT
<213> ORGANISM: Artificial Sequence
<220> FEATURE:
<223> OTHER INFORMATION: CA9 (Carbonic Anhydrase Peptide 9)

<400> SEQUENCE: 9

Arg Val Phe Lys Arg Tyr Lys Arg Trp Leu His Val Ser Arg Tyr Tyr
1               5                   10                  15

Phe Gly Ser Cys
            20

<210> SEQ ID NO 10
<211> LENGTH: 20
<212> TYPE: PRT
<213> ORGANISM: Artificial Sequence
<220> FEATURE:
<223> OTHER INFORMATION: CA10 (Carbonic Anhydrase Peptide 10)

<400> SEQUENCE: 10

Trp Arg Trp Trp His Trp His Trp Lys Arg Arg Trp Pro His Arg His
1               5                   10                  15

Arg Gly Ser Cys
            20

<210> SEQ ID NO 11
<211> LENGTH: 20
<212> TYPE: PRT
```

```
<213> ORGANISM: Artificial Sequence
<220> FEATURE:
<223> OTHER INFORMATION: CA11 (Carbonic Anhydrase Peptide 11)

<400> SEQUENCE: 11

Ile Glu Asp Thr Tyr Leu Arg Phe Arg His Tyr Gly Trp Tyr Asn Asn
1               5                   10                  15

Asn Gly Ser Cys
            20

<210> SEQ ID NO 12
<211> LENGTH: 20
<212> TYPE: PRT
<213> ORGANISM: Artificial Sequence
<220> FEATURE:
<223> OTHER INFORMATION: CA12 (Carbonic Anhydrase Peptide 12)

<400> SEQUENCE: 12

Ser Ile Gly Ile Tyr Gly His Ala Ile Ala Arg Pro Gly Gly Trp Tyr
1               5                   10                  15

Phe Gly Ser Cys
            20

<210> SEQ ID NO 13
<211> LENGTH: 20
<212> TYPE: PRT
<213> ORGANISM: Artificial Sequence
<220> FEATURE:
<223> OTHER INFORMATION: CA13 (Carbonic Anhydrase Peptide 13)

<400> SEQUENCE: 13

Tyr Pro Ala Asn Thr Trp Lys Trp Leu Asn Ala Trp Ala Val Phe Ile
1               5                   10                  15

Pro Gly Ser Cys
            20

<210> SEQ ID NO 14
<211> LENGTH: 20
<212> TYPE: PRT
<213> ORGANISM: Artificial Sequence
<220> FEATURE:
<223> OTHER INFORMATION: Comparison attachment peptide (14)

<400> SEQUENCE: 14

Glu Ser Val Pro Thr Asp Leu Pro Met Asp Thr Met Glu Gly Lys Asn
1               5                   10                  15

Trp Gly Ser Cys
            20
```